United States Patent
Dolan et al.

(10) Patent No.: US 8,726,917 B2
(45) Date of Patent: May 20, 2014

(54) STRETCH FLOSS BAND

(75) Inventors: John W. Dolan, Wilmington, DE (US); Michael F. Altman, Kennett Square, PA (US); Donald L. Hollenbaugh, Jr., North East, MD (US); Rachel Radspinner, Flagstaff, AZ (US); Alex R. Hobson, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/252,585

(22) Filed: Oct. 4, 2011

(65) Prior Publication Data

US 2013/0081648 A1    Apr. 4, 2013

(51) Int. Cl.
*A61C 15/04*    (2006.01)

(52) U.S. Cl.
USPC ............................................ 132/321; 132/323

(58) Field of Classification Search
USPC ............. 132/321, 329, 323, 324, 327; 433/23
See application file for complete search history.

(56) References Cited

U.S. PATENT DOCUMENTS

| | | | | |
|---|---|---|---|---|
| 3,247,857 A | * | 4/1966 | Kanbar | 132/329 |
| 3,953,566 A | | 4/1976 | Gore | |
| 4,550,741 A | * | 11/1985 | Krag | 132/321 |
| 4,836,226 A | * | 6/1989 | Wolak | 132/321 |
| 5,518,012 A | * | 5/1996 | Dolan et al. | 132/321 |
| 5,566,691 A | * | 10/1996 | Dolan et al. | 132/321 |
| 5,708,044 A | | 1/1998 | Branca | |
| 5,819,769 A | * | 10/1998 | Gutierrez | 132/327 |
| 5,947,132 A | * | 9/1999 | Swanson | 132/321 |
| 6,055,993 A | * | 5/2000 | Meyer et al. | 132/323 |
| 6,161,555 A | * | 12/2000 | Chen | 132/321 |
| 6,340,027 B1 | * | 1/2002 | Hagne et al. | 132/321 |
| 6,371,133 B1 | * | 4/2002 | Gant | 132/321 |
| 6,539,951 B2 | * | 4/2003 | Baillie et al. | 132/321 |
| 6,541,589 B1 | * | 4/2003 | Baillie | 526/250 |
| 7,521,010 B2 | * | 4/2009 | Kennedy et al. | 264/113 |
| 7,531,611 B2 | | 5/2009 | Sabol et al. | |
| 2003/0172951 A1 | * | 9/2003 | Baillie et al. | 132/321 |
| 2003/0196676 A1 | * | 10/2003 | Baillie et al. | 132/321 |
| 2005/0016563 A1 | * | 1/2005 | Prins | 132/321 |
| 2005/0257801 A1 | * | 11/2005 | Kayser | 132/200 |

(Continued)

FOREIGN PATENT DOCUMENTS

WO    WO 92/06648    4/1992

OTHER PUBLICATIONS

International Search Report—PCT/US2012/057557 dated Mar. 28, 2013.

*Primary Examiner* — Robyn Doan
*Assistant Examiner* — Tatiana Nobrega
(74) *Attorney, Agent, or Firm* — Allan M. Wheatcraft

(57) ABSTRACT

A dental cleaning article comprising a band of expanded fluoropolymer that is highly distensible at room temperature, such that it can be stretched from a first state to a second state is described. The diameter of the band of expanded fluoropolymer may be increased by stretching by, in some embodiments, two times or more the original first state diameter. Likewise the cross sectional area of the band of expanded fluoropolymer may be reduced upon stretching to less than one quarter the first state cross sectional area. The band of expanded fluoropolymer provides the user with the ability to stretch the band a desired amount, such that they may more effectively clean between their teeth. Furthermore, the band may be regular or irregularly shaped, and in some embodiments may comprise higher density regions.

27 Claims, 27 Drawing Sheets

(56) References Cited

U.S. PATENT DOCUMENTS

| | | |
|---|---|---|
| 2006/0105179 A1 | 5/2006 | Hofman |
| 2006/0147869 A1 | 7/2006 | Hekimian |
| 2007/0087310 A1 | 4/2007 | Giusti |
| 2007/0131242 A1* | 6/2007 | Fleck .......................... 132/321 |
| 2007/0204877 A1* | 9/2007 | Dolan et al. ................. 132/321 |
| 2008/0017218 A1* | 1/2008 | Lutz et al. ................... 132/321 |
| 2008/0053892 A1* | 3/2008 | Bacino et al. ................ 210/483 |
| 2009/0020134 A1* | 1/2009 | Tomsic et al. ............... 132/327 |
| 2009/0032470 A1* | 2/2009 | Bacino et al. ................ 210/650 |
| 2009/0093602 A1 | 4/2009 | Ford |
| 2010/0248324 A1 | 9/2010 | Xu et al. |
| 2011/0155168 A1* | 6/2011 | Chung ......................... 132/327 |

* cited by examiner

STRETCH FLOSS BAND

FIELD OF THE INVENTION

The invention relates to dental cleaning articles and in one embodiment to a band of expanded fluoropolymer that is highly distensible at room temperature such that it can be stretched from a first state to a second state. The band of expanded fluoropolymer may be more easily held and manipulated than a strand of material for flossing between teeth.

BACKGROUND OF THE INVENTION

Expanded fluoropolymer provides many advantages over conventional material for dental cleaning. One advantage is the low friction characteristics of expanded fluoropolymer, which allows it to more easily glide through tight teeth. This low friction however, makes it difficult to grip and hold during flossing. The expanded fluoropolymer strands currently available come in various sizes and density. Unfortunately, many people have a wide range of gaps between their teeth and one size, density, or type of floss may not adequately clean between all their teeth.

There exists a need for an expanded fluoropolymer dental cleaning article that is easy to hold and can effectively clean a wide range of gaps between teeth.

SUMMARY OF THE INVENTION

The invention is directed to a dental cleaning article comprising a band of expanded fluoropolymer that is distensible from a first state to a second stretched state. In one embodiment, the circumference of the band of expanded fluoropolymer is increased by a factor of at least two, from the first state to the second stretched state. Likewise, in one embodiment the cross sectional area of the band in the second stretched state is one quarter or less of the cross-sectional area of the band in the first state.

In one embodiment, the microstructure of the expanded fluoropolymer comprises nodes and interconnecting fibrils wherein the nodes have an aspect ratio that changes from the first state to the second stretched state. The aspect ratio in the second stretched state is in one embodiment, at least two times greater than the aspect ratio of the nodes in the first state.

The band of expanded fluoropolymer in one embodiment consists essentially of a seamless tube section, and in another embodiment the band comprises at least one strip of material attached to form a band having one or more seams. In yet another embodiment, the band comprises a section of material having a slit or shaped opening, such as a circle or oval and is a referred herein as a sheet band. The sheet band may have a regular or irregular shape and in one embodiment has a generally rectangular outer shape. In another embodiment, the sheet band has a circular or oval outer shape, and a slit or shaped opening, such as a circle or oval.

The band of expanded polymer may have a generally consistent cross section around the circumference, or it may have a variable cross section. In one embodiment, at least one region of the band of expanded fluoropolymer has a higher density than an adjacent region. The band may be compressed or imbibed with another material to produce these higher density regions. In another embodiment, the band may be compressed in at least one region to provide a larger surface region that may be used to facilitate stretching the band to a second state. In yet another embodiment, additional material is attached or detachably attached to the band for stretching and or handling, such as but not limited to another polymer film.

The dental cleaning article may also comprise wax or other additional material on one or more surfaces. Wax may increase the friction of the band and increase dental cleaning performance. In addition, the wax or other material may be continuous on discontinuous. In one embodiment, the wax or other material is continuous in the first state, but becomes discontinuous after the band is stretched to a second state. In yet another embodiment additional material is incorporated at least partially into the expanded fluoropolymer such as an imbibed material or filler material.

The dental cleaning article may be supported on a support device and in some embodiments the support device provides the user with a means to stretch the band. The support device in one embodiment may comprise a pair of support members connected at a pivot point, and a distensible band securing portion. The securing portion may comprise a recess in the support member. The user may squeeze the support members such that they move about the pivot and stretch the band.

Numbers used to indicate a feature or element in a figure are used consistently throughout all figures.

DETAILED DESCRIPTION OF THE INVENTION

Figure 1A:
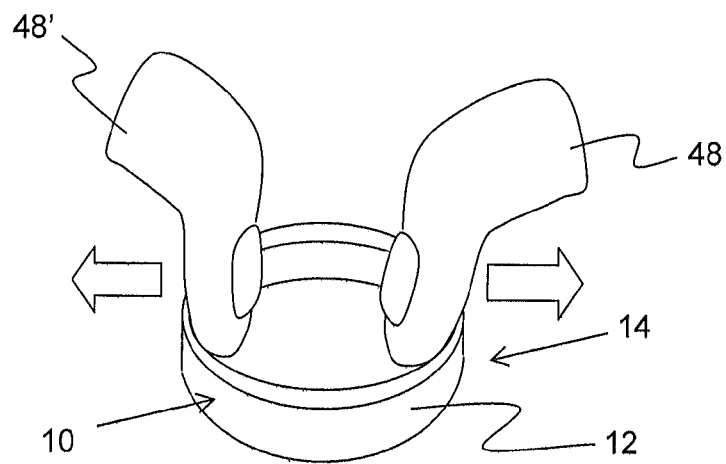
FIG. 1A shows an isometric view of one embodiment of a dental cleaning article wherein the band of expanded fluoropolymer is a tube section in a first state.
Figure 1B:
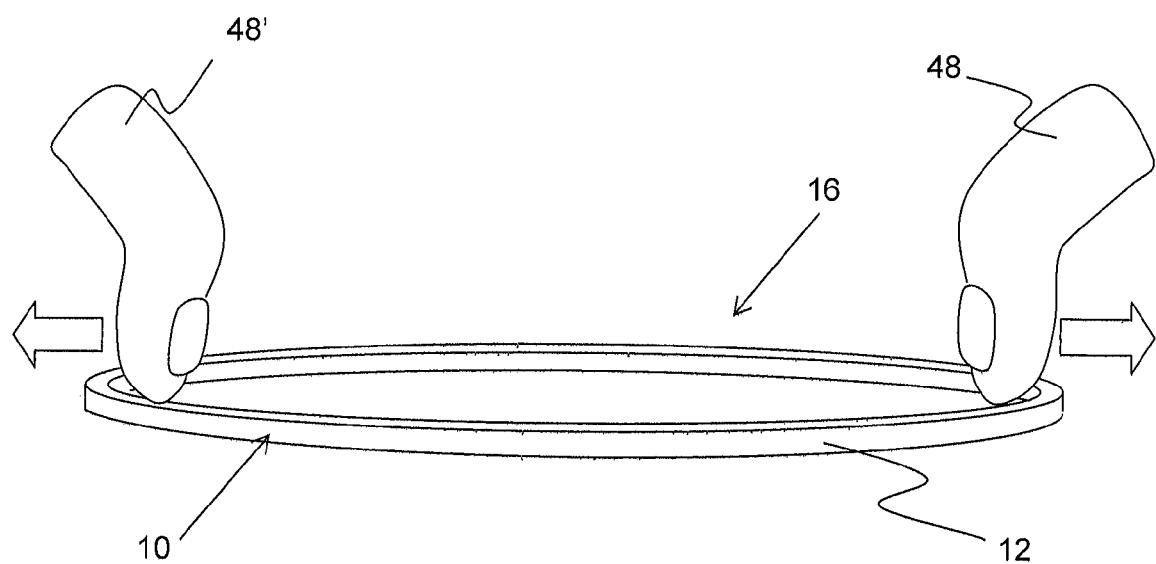
FIG. 1B shows an isometric view of one embodiment of a dental cleaning article wherein the band of expanded fluoropolymer is in a second stretched state.

The dental cleaning article 10 of the present invention comprises a band of expanded fluoropolymer 12 having a first state 14 and a second stretched state 16 as shown in FIG. 1A and FIG. 1B respectively. The band configuration is a more easily held and manipulated form than a strand of floss. Providing the band in a first state to the user allows them to stretch the band a desirable amount for handling, and to accommodate the gaps between their teeth. The circumference of the band in the second stretched state may be at least two times greater than the circumference of the band in the first state. The circumference as used herein is defined as the length of the inside surface of the band. In addition, the cross sectional area of the band in the second stretched state may be one quarter or less of the cross-sectional area of the band in the first state.

The band of expanded fluoropolymer can be stretched manually, by inserting fingers 48 and 48' into the band 12 and pulling to increase the circumference of the band, as depicted in FIG. 1A and FIG. 1B. A benefit of this method to form a dental cleaning article is that a user can stretch the band to a desirable circumference. In addition, the cross sectional area of the dental cleaning article can be controlled by a user to accommodate the variation in gaps between teeth. For example, a user may choose to stretch a band of expanded fluoropolymer to a second stretched state to accommodate larger gaps in-between their teeth, and then further stretch the band to reduce the cross-sectional area to accommodate the narrow gaps between their teeth.

In one embodiment, the band of expanded fluoropolymer is made from porous expanded polytetrafluoroethylene (PTFE), for instance as generally described in U.S. Pat. No. 3,953,566 to Gore. The expandable fluoropolymer may comprise in one embodiment, PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al. The expanded fluoropolymer of the present invention may comprise any suitable microstructure for achieving the desired combination of properties required, such as but not limited to, strength, matrix tensile strength, percent elongation, extension, density, and abrasion resistance as described herein. In one embodiment, the expanded fluoropolymer may comprise a microstructure of nodes interconnected by fibrils such as described in U.S. Pat. No. 3,953,566 to Gore. In a preferred embodiment, the expanded fluoropolymer comprises expanded PTFE and in another embodiment, the expanded fluoropolymer consists essentially of PTFE.

Figure 2A:
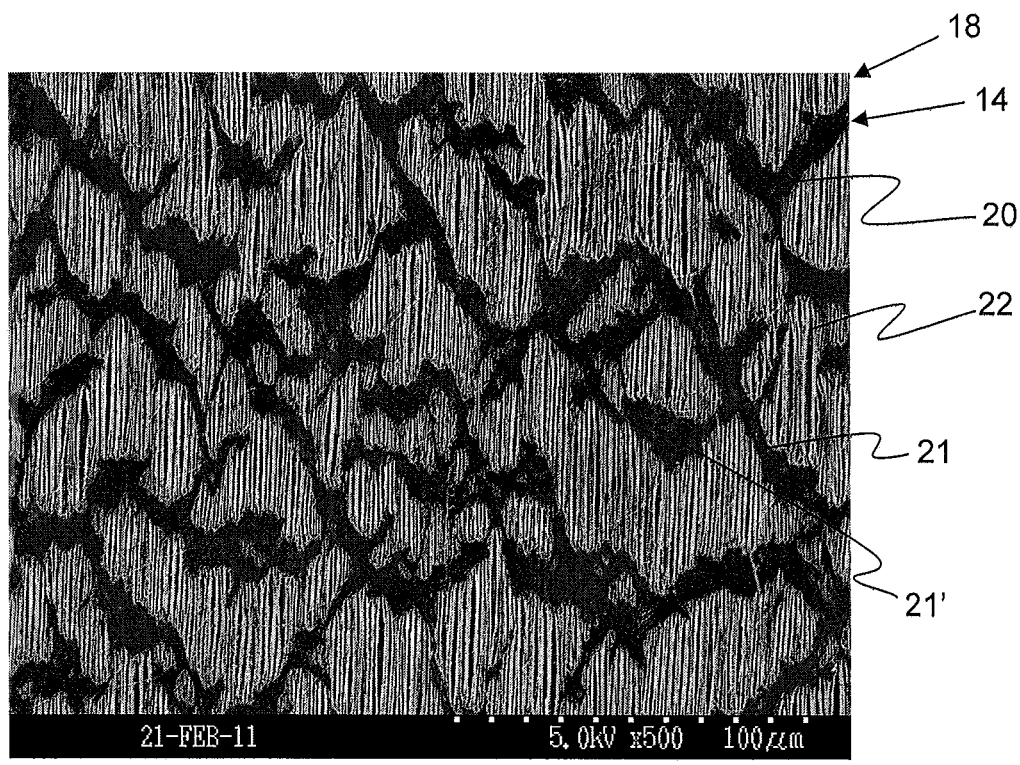
FIGS. 2A, 2C, 2E, 2G, and 2I are surface scanning electron micrographs (SEM) of the outside surface of a band of expanded fluoropolymer in a first state.
Figure 2B:
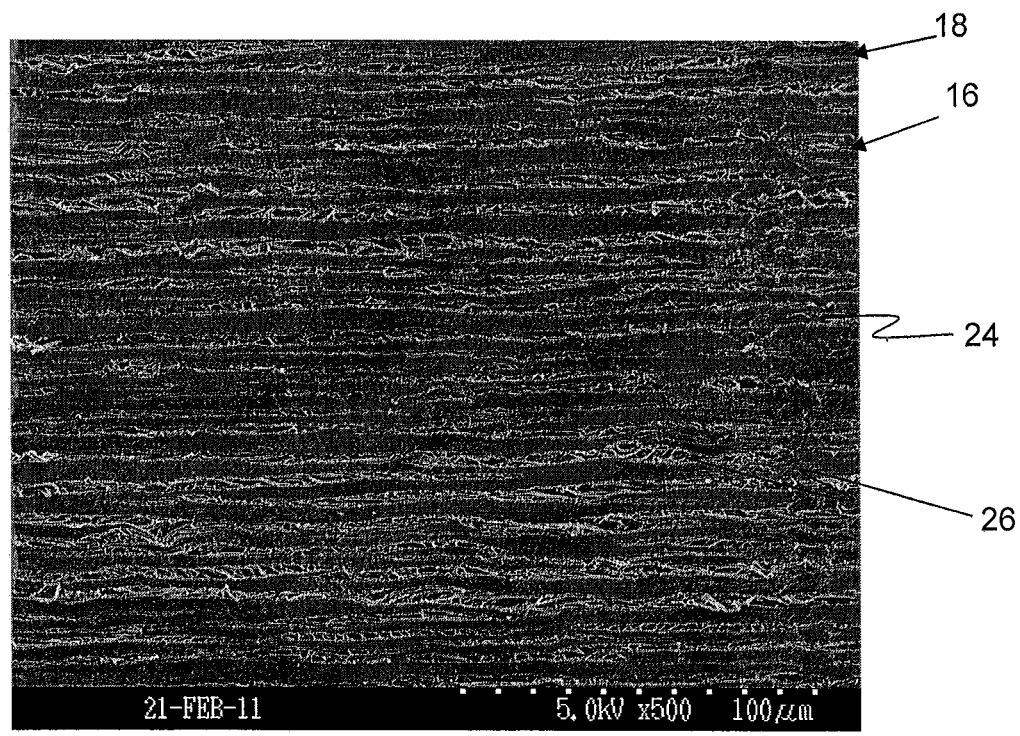
FIGS. 2B, 2D, 2F, 2H, and 2J are surface SEMs of the outside surface of a band of expanded fluoropolymer in a second stretched state.

The expanded fluoropolymer shown in the surface SEM 18 of FIG. 2A and FIG. 2B, comprises nodes 20, 24 and interconnecting fibrils 22, 26. FIG. 2A is a surface SEM of expanded fluoropolymer in the first state 14 and FIG. 2B is a surface SEM of expanded fluoropolymer in a second stretched state 16. The nodes 20 in FIG. 2A are irregularly shaped and many are branched or have multiple connecting portions 21 and 21' for example. As shown in FIG. 2B, the nodes 24 in a second stretched state are at least two times the aspect ratio of the nodes in the first state and are aligned essentially parallel with each other. The aspect ratio of a node as used herein is defined as the ratio of the length of a node, as measured across the longest dimension, divided by the width of the same node measured orthogonally to the length. The aspect ratio of nodes in a second stretched state may be greater than 10, 20, 50, 100, or 200, or between 10 and 200, 20 and 100, or between 10 and 50. The change in the aspect ratio of the nodes from the first state to the second stretched state can be greater than 2, 4, 8, 12 or between 2 and 12, 2 and 8, or between 2 and 4.

Figure 3A:
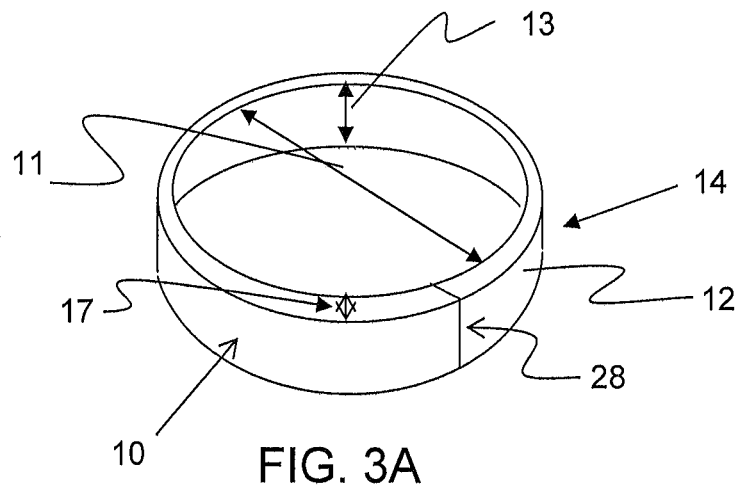
FIG. 3A shows an isometric view of a band of expanded fluoropolymer having a seam.
Figure 3B:
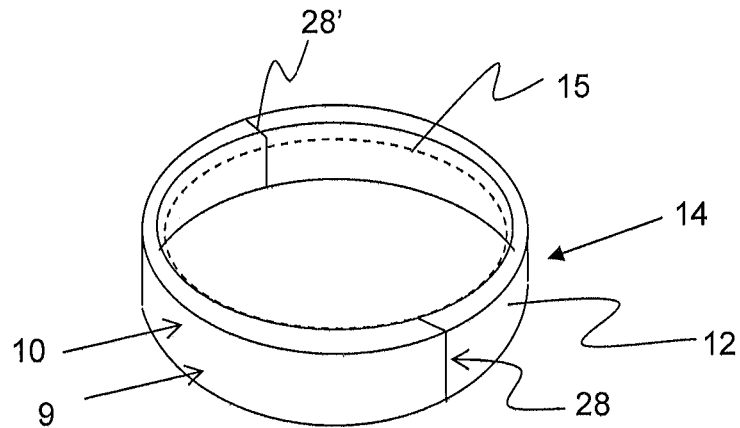
FIG. 3B shows an isometric view of a band of expanded fluoropolymer having two seams.
Figure 3C:
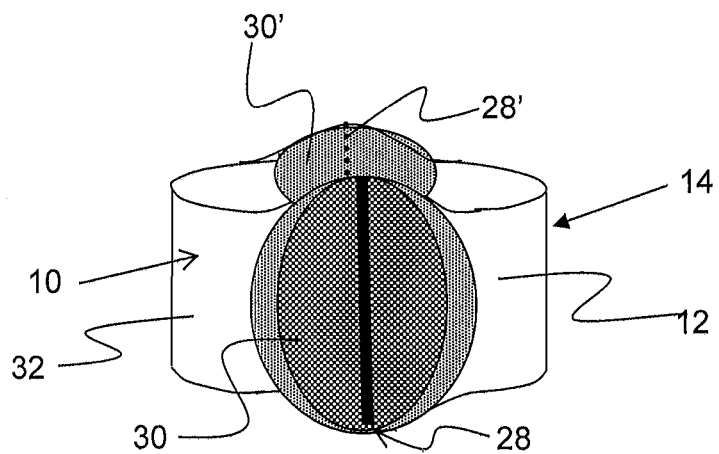
FIG. 3C shows a band of expanded fluoropolymer having two seams and high density regions.

The dental cleaning article as described herein comprises a band of expanded fluoropolymer that may be formed from a single piece of material, as depicted in FIG. 1, comprise a single piece of material having a seam 28, as depicted in FIG. 3A, or may comprise two or more attached pieces of expanded fluoropolymer as depicted in 3B and 3C. FIGS. 3B and 3C show a band formed from two pieces of material having two seams 28 and 28'. The expanded fluoropolymer may be attached through any conventional means including but not limited to, the use of adhesives, ultrasonic bonding, thermal welding, or the combination of any of these methods, and the like. The band depicted in FIG. 3C comprises two high density regions 30, 30' around the seams 28, 28'. In one embodiment, the high density regions are formed when heat and pressure are used to attach pieces of expanded fluoropolymer to form the band. In another embodiment, the high density region is formed when adhesive or another material at least partially fills the voids or pores in the expanded fluoropolymer. Alternatively, an additional material may be used to attach one or more pieces of expanded fluoropolymer to form a band.

Figure 4A:
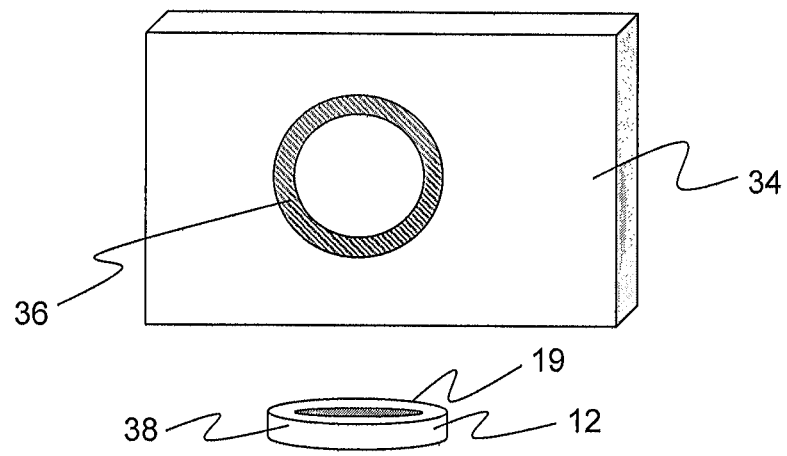
FIG. 4A shows an isometric view of a sheet band of expanded fluoropolymer cut from a sheet of material.
Figure 4B:
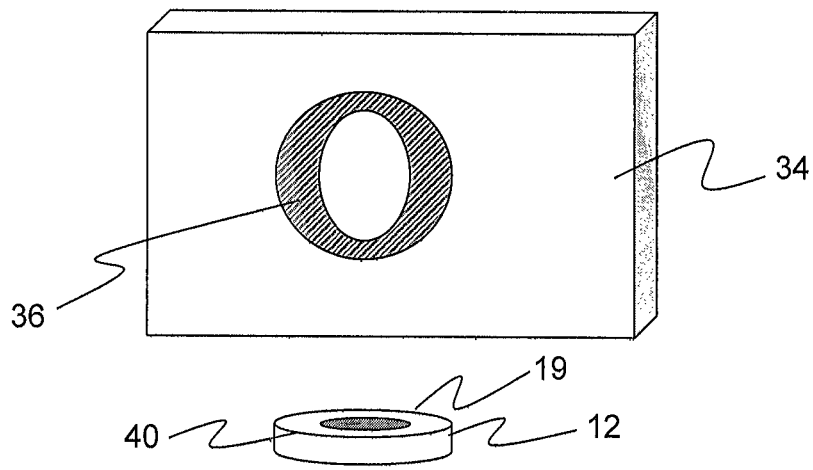
FIG. 4B shows an isometric view of an irregularly shaped sheet band of expanded fluoropolymer cut from a sheet of material.
Figure 4C:
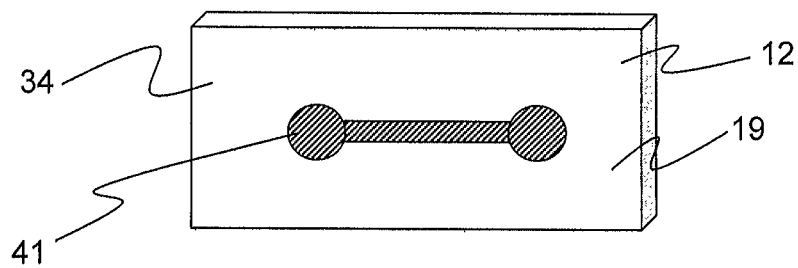
FIG. 4C shows an isometric view of a sheet band of expanded fluoropolymer having an irregularly shaped opening.

The dental cleaning article in one embodiment comprises a generally tubular section configuration, having a width 13, thickness 17, inner diameter 11 and circumference 15 as depicted in FIGS. 3A and 3B. In some embodiments, the distensible band of expanded fluoropolymer 12 may be in the form of a sheet band 19, and be formed from a sheet or sheets of expanded fluoropolymer 34 as depicted in FIG. 4A, and FIG. 4B. In one embodiment, multiple sheets of expanded fluoropolymer are attached either to other expanded fluoropolymers, or to other materials. It is envisioned that any shaped sheet band may be formed including regular shaped articles such as a circle, as depicted in FIG. 4A, or irregular shaped articles 40, as depicted in FIG. 4B. The shape formed from the sheet of expanded fluoropolymer is shown by the cut out region 36 in both FIGS. 4A and 4B. A rectangular or square outer shaped sheet band may also be formed as depicted in FIG. 4C, having an irregularly shaped opening 41 defining the inner surface of the band.

The inner diameter of the distensible band 9 may be determined by measuring the length of the inner circumference or inner surface and dividing by the constant pi as depicted in FIGS. 3A and 3B. Expanded fluoropolymer in many embodiments is not rigid and the distensible band may not have a freestanding tubular shape. The circumference of the band as used herein refers to the inner circumference and can be measured by cutting the band from the outer surface to inner surface and measuring the length along the inner surface. The inner surface of the band may be irregularly shaped such as shown in FIG. 4C, however the same method may be followed to measure the effective circumference and effective diameter.

The distensible band may have any suitable dimensions, and in some embodiments, the inner diameter is large enough to allow for the insertion of a finger or fingers into the band and subsequently stretch it. In these embodiments, the inner diameter of the band may be greater than about 10 mm, or between 10 and 25 mm, 10 and 50 mm, or between 10 and 75 mm. In other embodiments, the inner diameter may be too small to allow for the insertion of a finger or fingers into the band, such as less than 10 mm, or between 3 mm and 10 mm, or between 5 mm and 10 mm. The width of the dental cleaning article may be selected to be greater than 0.50 mm and less than 1.5 mm, 3.0 mm, 10 mm, 15 mm, or 25 mm, or between 3 mm and 25 mm, or between 3 mm and 15 mm.

In some embodiments, the distensible band in the first state may be effectively unsuitable for use as a dental cleaning article. For example, the inner diameter or circumference may be too small for the distensible band to be effectively manually manipulated as a dental cleaning article. For example, distensible bands with an inner diameter of less than 10 mm or in some cases less than 20 mm are considered too small to be effectively manually manipulated as a dental cleaning article. Likewise, in some embodiments, the width or thickness of the band may be too large in the first state for the distensible band to be effectively used as a dental cleaning article. For example, when the width or thickness of the distensible band is greater than about 5 mm, the band may not be useful as a dental cleaning article, as it may be too large to fit between the gaps in-between teeth. In these embodiments, the distensible band only becomes effectively useful as a dental cleaning article after being stretched to a second stretched state.

Figure 5A:
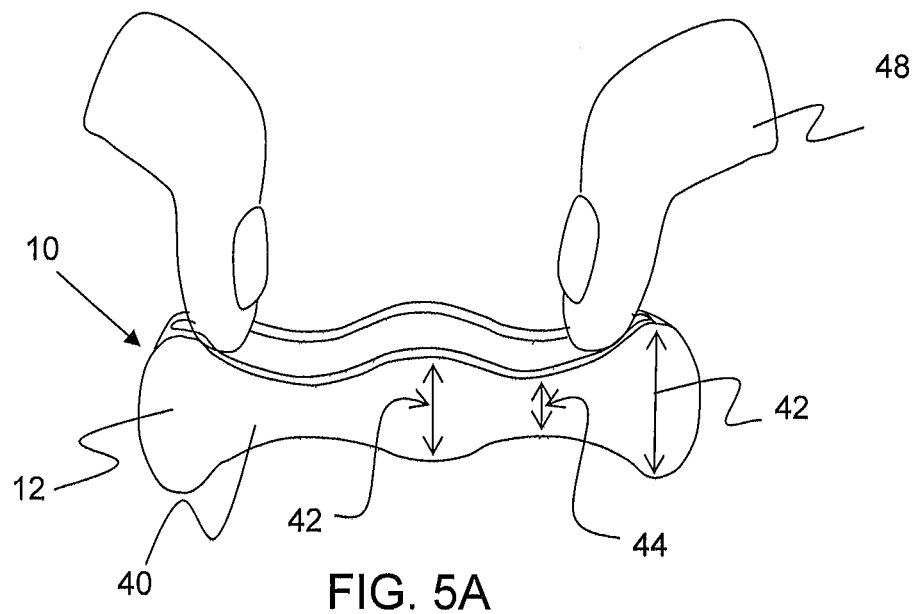
FIG. 5A shows an isometric view of an irregularly shaped band of expanded fluoropolymer in a first state.
Figure 5B:
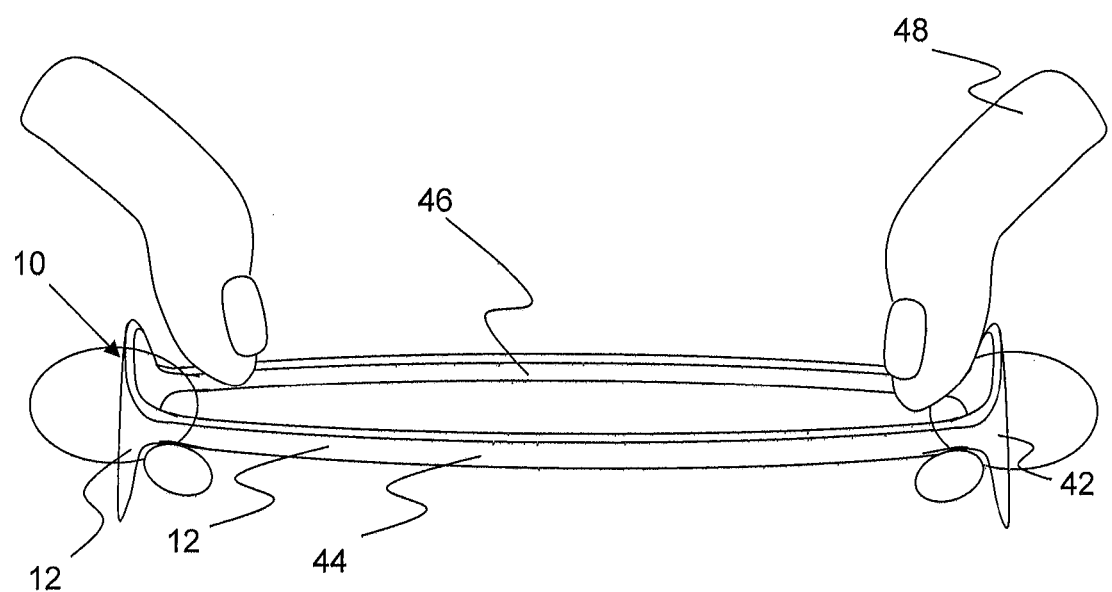
FIG. 5B shows an irregularly shaped band of expanded fluoropolymer in a second stretched state.

The band of expanded fluoropolymer may have any irregular shape, such as that shown in FIG. 5A. The dental cleaning article 10 shown in FIG. 5A, comprises wider portions 42, and more narrow portions 44 around the circumference of the band. A user may preferably place their fingers along a wider portion of the band for stretching. The wider portions may provide less stress on the user's fingers as the band is stretched from the first state to a second state. In addition, as depicted in FIG. 5B, the wider portions 42 under the fingers 48, may remain wider, and in some cases significantly wider, such as more than 2 or 3 times wider, than the stretched portion of the band 46. Width, as used herein in reference to a band dimension, is a measure of the widest dimension of the material essentially perpendicular to the circumference.

Figure 6A:
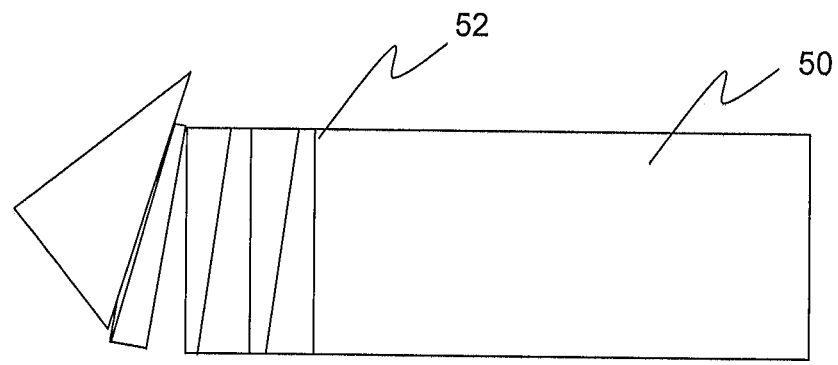
FIG. 6A shows a side view tube of expanded fluoropolymer having cut lines therein.
Figure 6B:
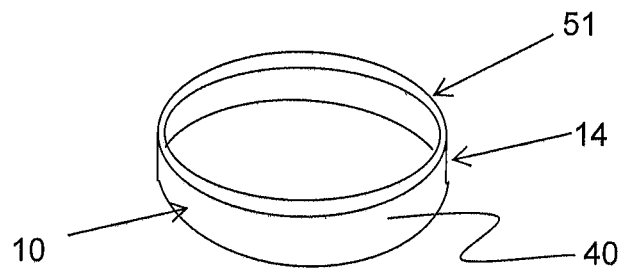
FIG. 6B shows an isometric view of a band of expanded fluoropolymer in a tube section in a first state having an irregular cross-section.
Figure 6C:
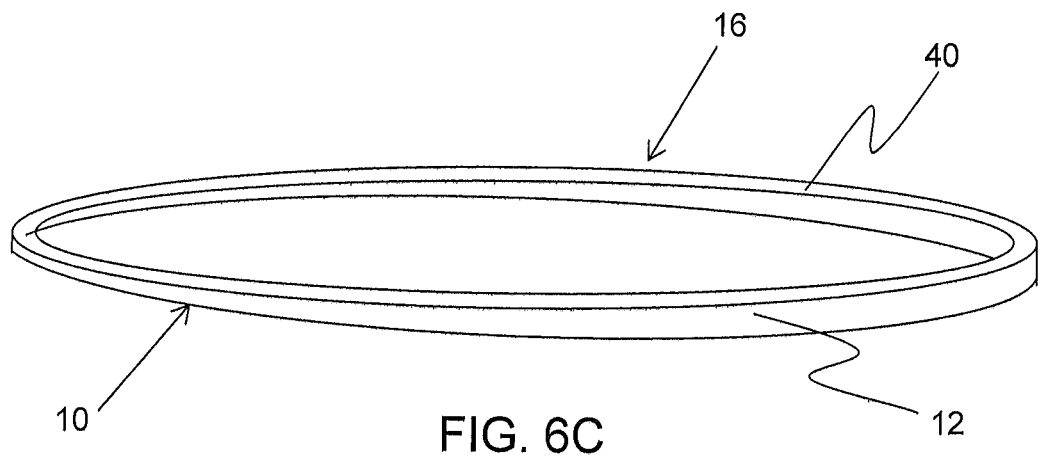
FIG. 6C shows an isometric view of a band of expanded fluoropolymer in a second stretched state.
Figure 7A:
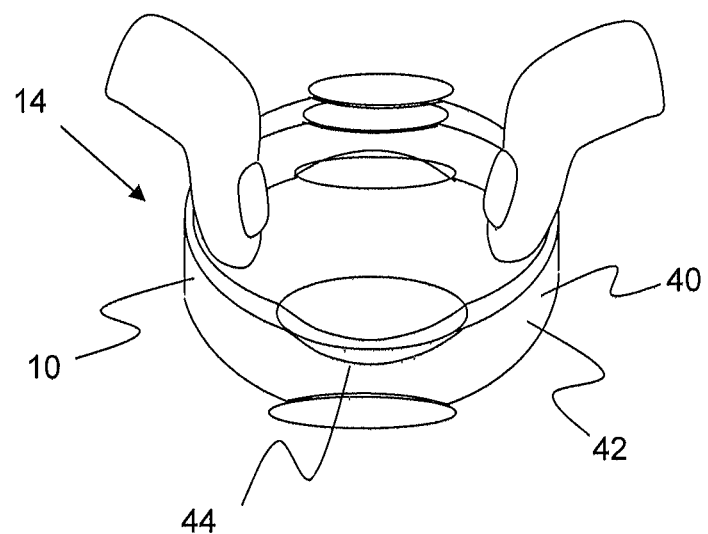
FIG. 7A shows an isometric view of a band of expanded fluoropolymer in a first state having an irregular shape.
Figure 7B:
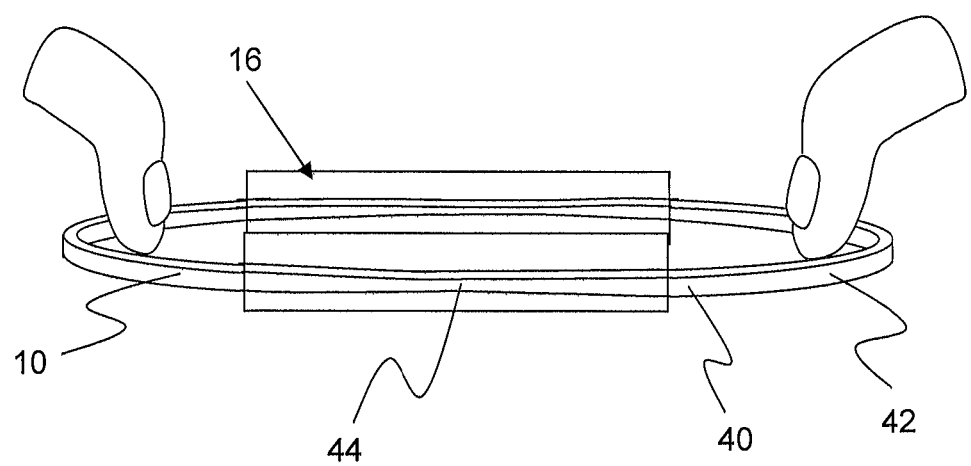
FIG. 7B shows an isometric view of a band of expanded fluoropolymer in a second state having an irregular shape.
Figure 8A:
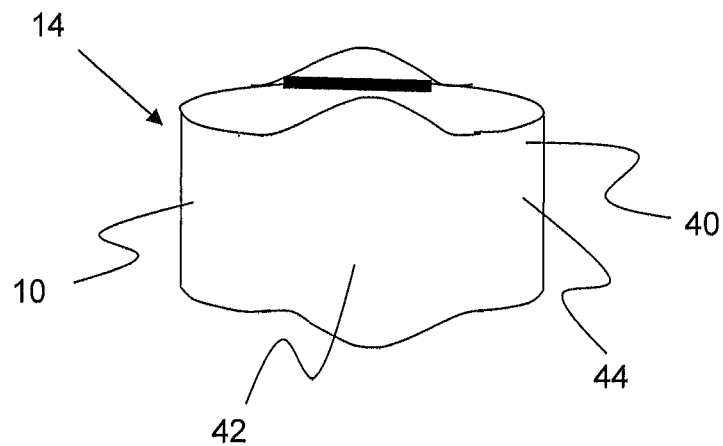
FIG. 8A shows a band of expanded fluoropolymer in a first state having an irregular shape.
Figure 8B:
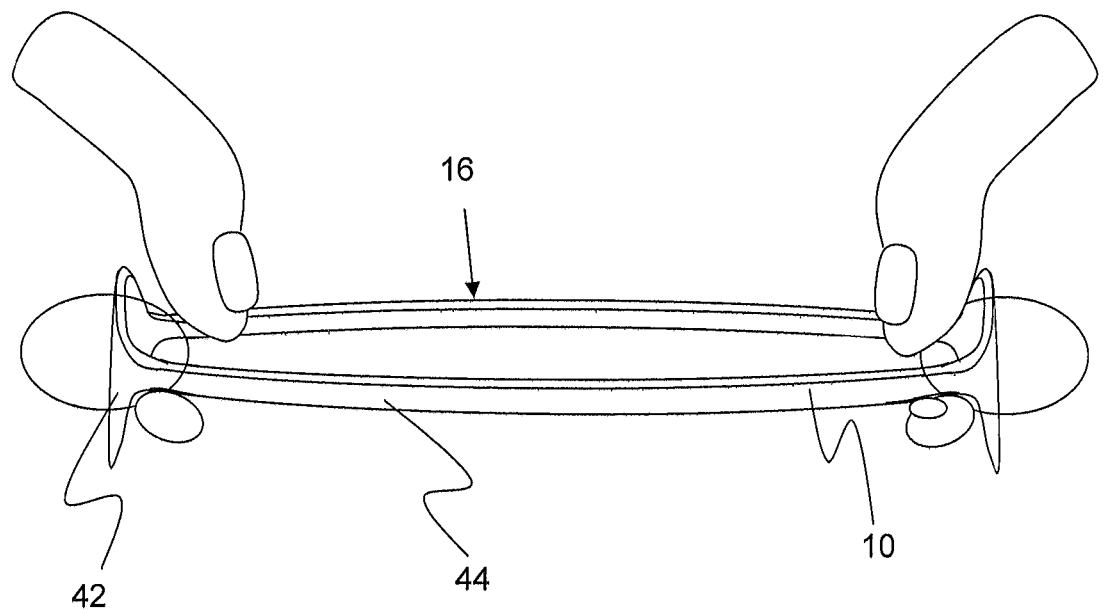
FIG. 8B shows an isometric view of a band of expanded fluoropolymer in a second state having an irregular shape.

The band of expanded fluoropolymer may be cut or otherwise formed from a tube 50 of expanded fluoropolymer as depicted in FIG. 6A, to form a seamless tube section 51. The tube may be cut to form regular shaped bands, or may be cut at an off angle to form irregular shaped bands as depicted in FIGS. 6A and 6B. The band shown in FIG. 6B when stretched to a second stretched state, as shown in FIG. 6C, may comprise larger and smaller cross sectional area portions. This variation in cross sectional area may allow for easier insertion into narrower gaps between teeth, and more effective cleaning between teeth having variable gaps. The dental cleaning article may be rotated by the user to provide an effective cross sectional area section of the band. FIGS. 7A, and 7B depict another embodiment wherein the band of floss has an irregular shape and variations in cross sectional area in both the first and second stretched states. FIGS. 8A and 8B show yet another embodiment wherein the band comprises an irregular shape having wider portions 42 and more narrow portions 44.

Figure 9A:
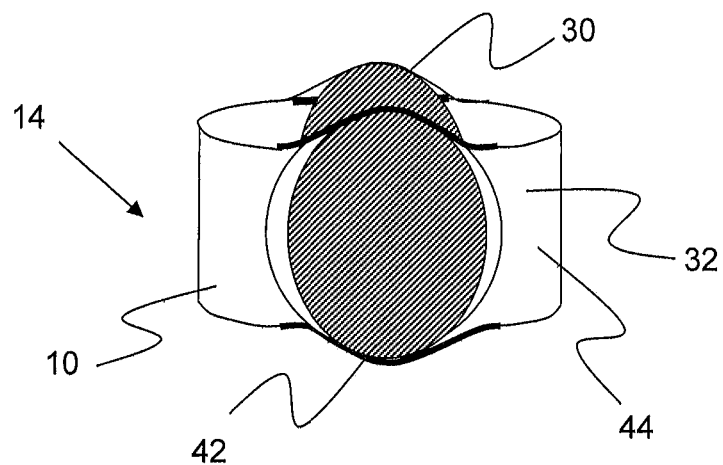
FIG. 9A shows an isometric view of a band of expanded fluoropolymer in a first state having an irregular shape and a high density region.
Figure 9B:
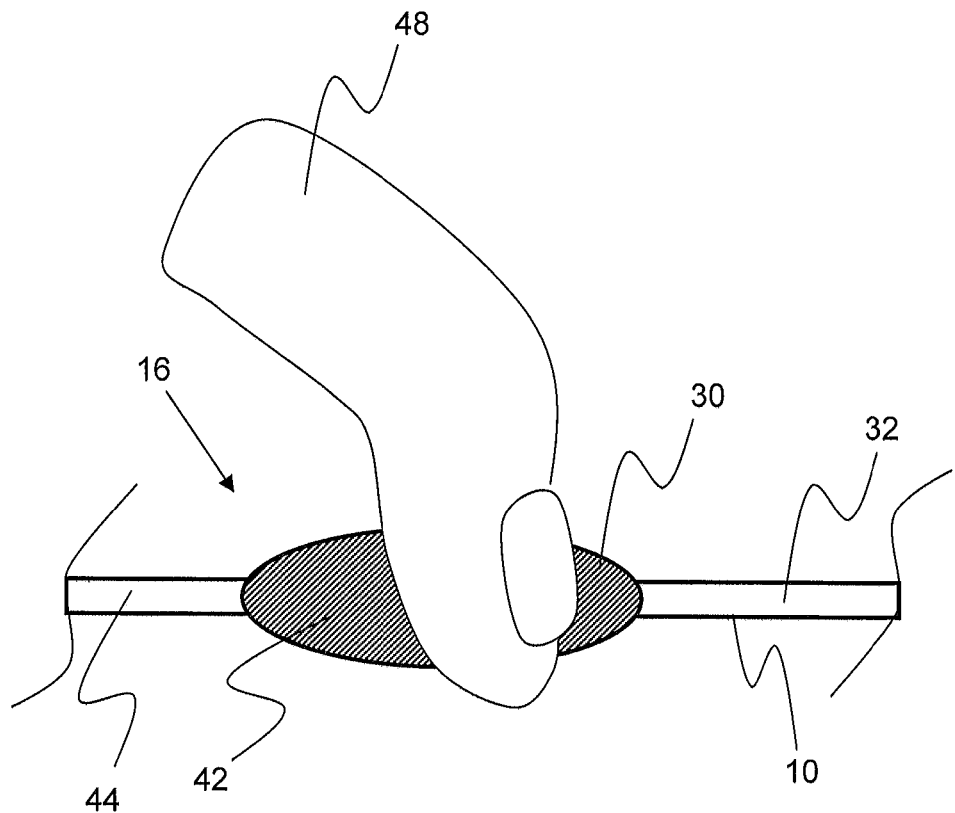
FIG. 9B shows an isometric view of a section of a band of expanded fluoropolymer in a second state having an irregular shape and a high density region.

FIG. 9A shows an irregularly shaped band of expanded fluoropolymer having high density regions, that provide the user with a wider portion from which to stretch the band. The large surface of the high density region 30 in contact with the user's finger 48 may provide for less stress and more comfort during the process of stretching the band from the first state to the second state, as depicted in FIG. 9B. In addition, additional material may be attached or imbibed into the dental cleaning article in at least one location to provide for improved grip of the band.

Figure 10A:
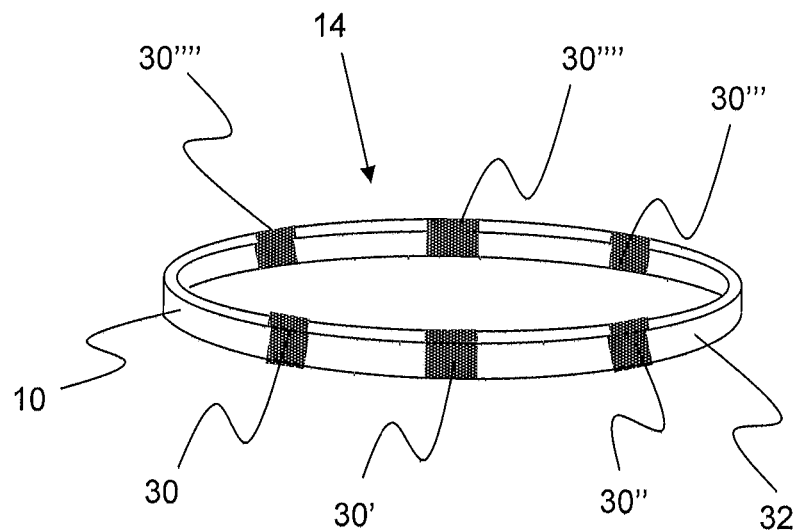
FIG. 10A shows an isometric view of a band of expanded fluoropolymer in a first state having multiple high density regions.
Figure 10B:
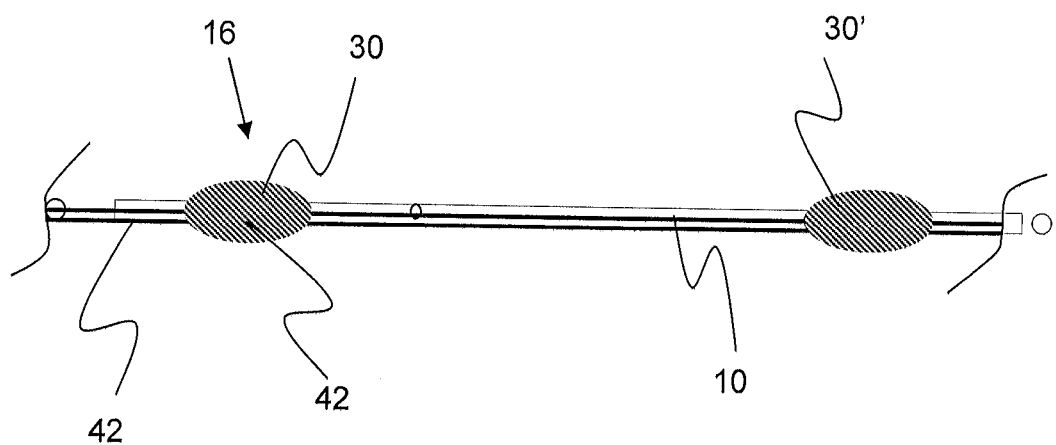
FIG. 10B shows a side view of a section of a band of expanded fluoropolymer in a second state having multiple high density regions

The dental cleaning article may comprise one more high density regions 30', 30'', 30''', that in one embodiment may stretch and deform less than adjacent lower density regions, resulting in a irregularly shaped band in the second stretched state, as depicted in FIG. 10A and FIG. 10B. The irregularly shaped band in the second state may provide for improved cleaning between teeth, wherein the larger or wider portions may act to more effectively scrub out and remove material between teeth. The high density regions may be formed by any conventional means including the application of heat and/or pressure, ultrasonic energy, addition of an additional material, in and/or on the band, or any combination of aforesaid means and the like. In an alternative embodiment, substantially all of the band is at a relatively high density, such as greater than 1.5 g/cc, 1.7 g/cc or greater than 2.0 g/cc in either the first or second stretched state.

Figure 11A:
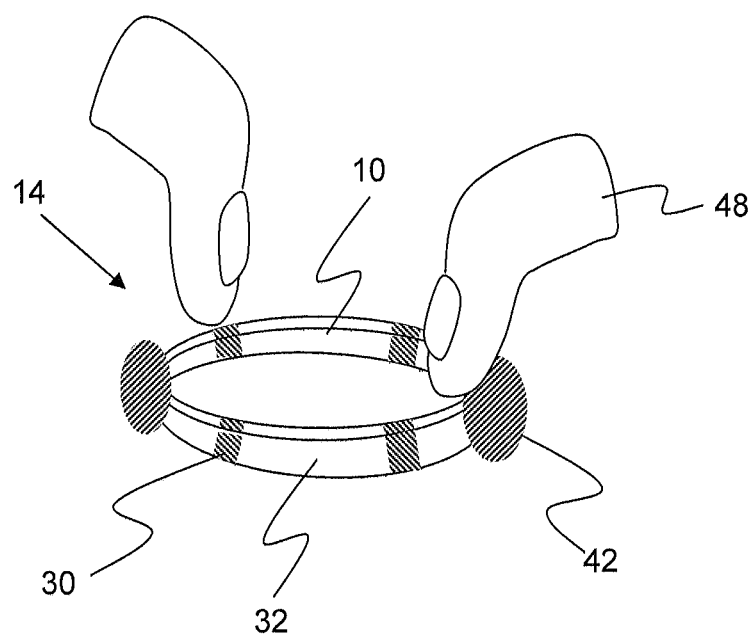
FIG. 11A shows an isometric view of a band of expanded fluoropolymer in a first state having a multiple high density regions, and an irregular cross-section.
Figure 11B:
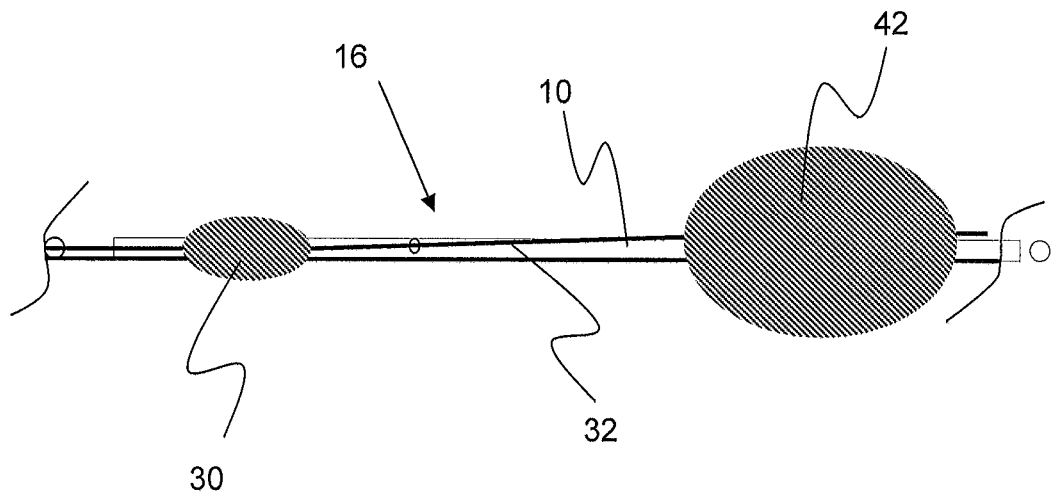
FIG. 11B shows a side view of a section of an irregularly shaped band of expanded fluoropolymer in a second state, having multiple high density regions.

The dental cleaning article may comprise a combination of features herein described, such as those shown in FIGS. 11A and 11B, where the irregularly shaped band 40, comprises wider portions 42, as well as high density region 30 and low density regions 32. In the second stretched state 16, the dental cleaning article 10 as shown in FIG. 11B has features for reduced pressure on the fingers, high density regions, low density regions, and wider portions for more effective cleaning between teeth.

Figure 12A:
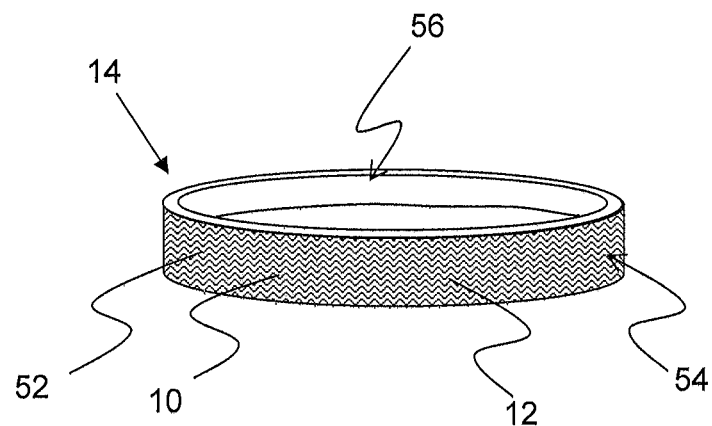
FIG. 12A show an isometric view of a band of expanded fluoropolymer with an additional material.
Figure 12B:
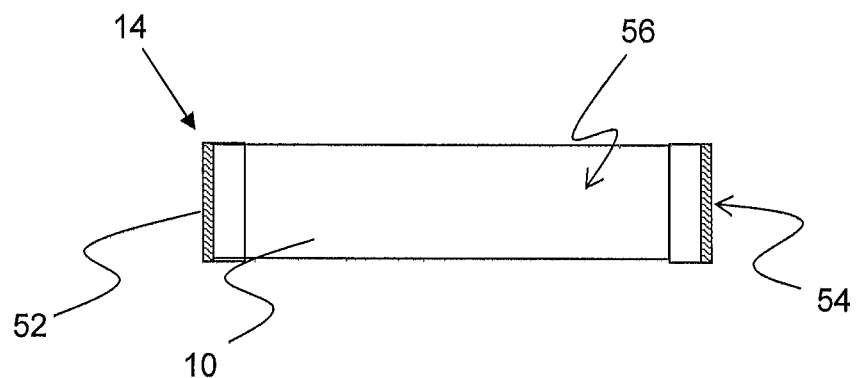
FIG. 12B shows a side view of a cross section of expanded fluoropolymer with an additional material on a portion of the surface.
Figure 12C:
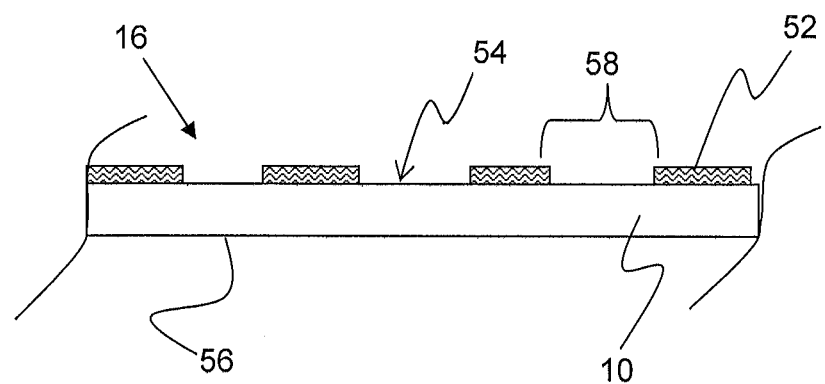
FIG. 12C shows a section of expanded fluoropolymer with an additional material being discontinuous on a portion of the surface.

In some embodiments, additional material may be incorporated into or on the dental cleaning article, including but not limited to, wax, flavor containing materials, such as mint, coloring materials, such as dyes or pigments, or abrasive materials, such filler particles, or combinations thereof and the like. The additional materials may be attached to one or more surfaces of the dental cleaning article or may be at least partially imbibed into or incorporated into the structure of the band, or expanded polymer or fluoropolymer. In one embodiment, an additional material 52, comprising a wax is attached to the outside surface 54 of a band of expanded fluoropolymer 12 as depicted in FIG. 12A, and cross sectional view in FIG. 12B. In one embodiment, the additional material 52 may become discontinuous 58 as the band is stretched from a first state to a second stretched state, as depicted in FIG. 12C. A wax or abrasive material may more effectively scrape and clean when in a discontinuous form.

Figure 13A:
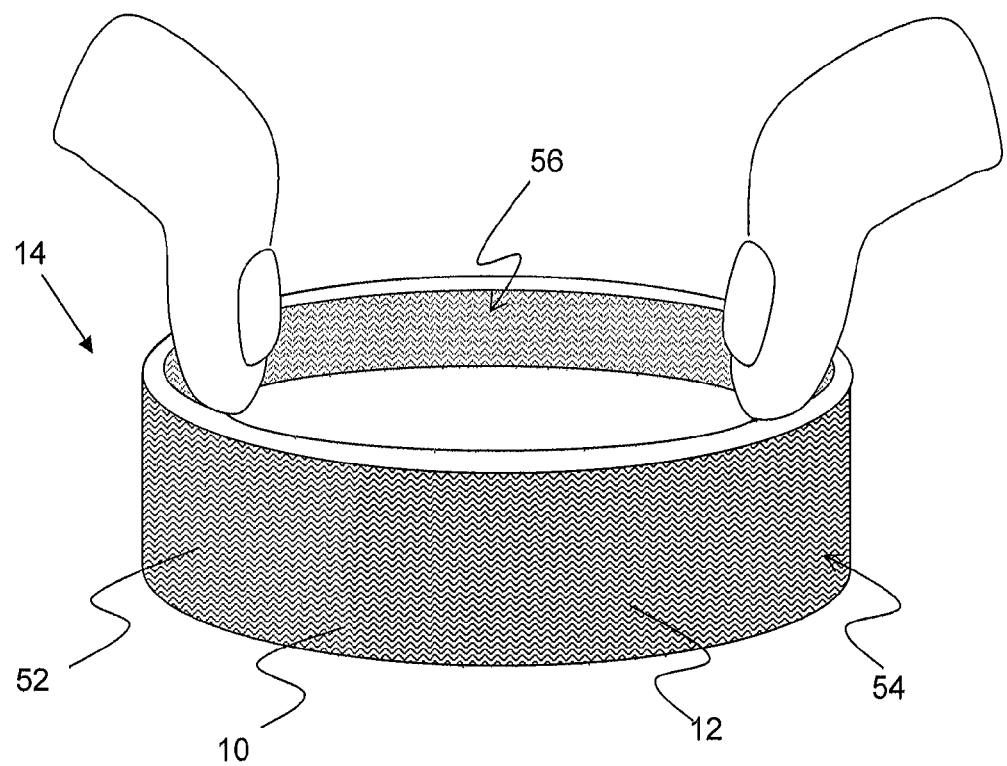
FIG. 13A shows an isometric view of a side view of a section of a band of expanded fluoropolymer with an additional material over essentially the entire surface.
Figure 13B:
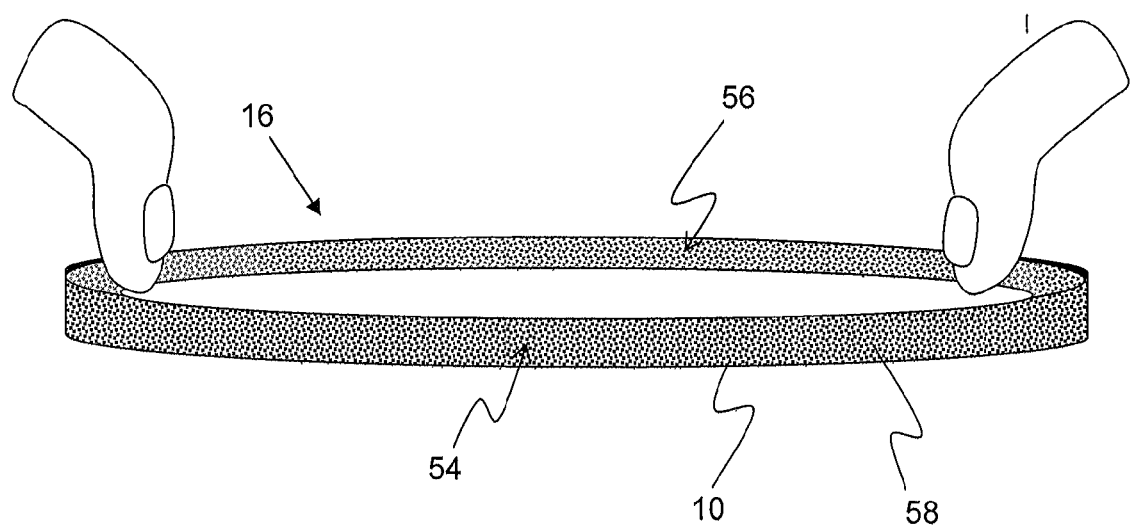
FIG. 13B shows an isometric view of a band of expanded fluoropolymer in a second stretched state, with an additional material being discontinuous.

In another embodiment, both the inside and outside surfaces of the band of expanded fluoropolymer comprise an additional material as depicted in FIGS. 13A and 13B. The additional material may in one embodiment be substantially continuous in the first state and become discontinuous in the second stretched state.

Figure 16:
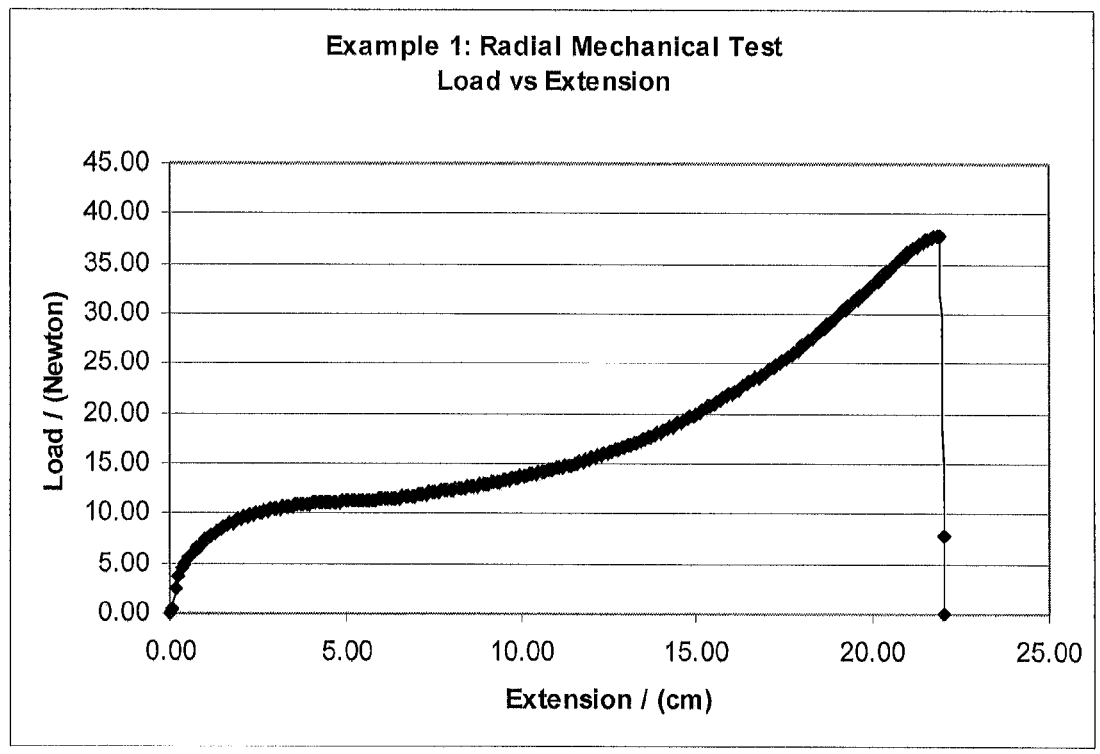
FIG. 16 shows a radial mechanical test response of example 1.
Figure 17A:
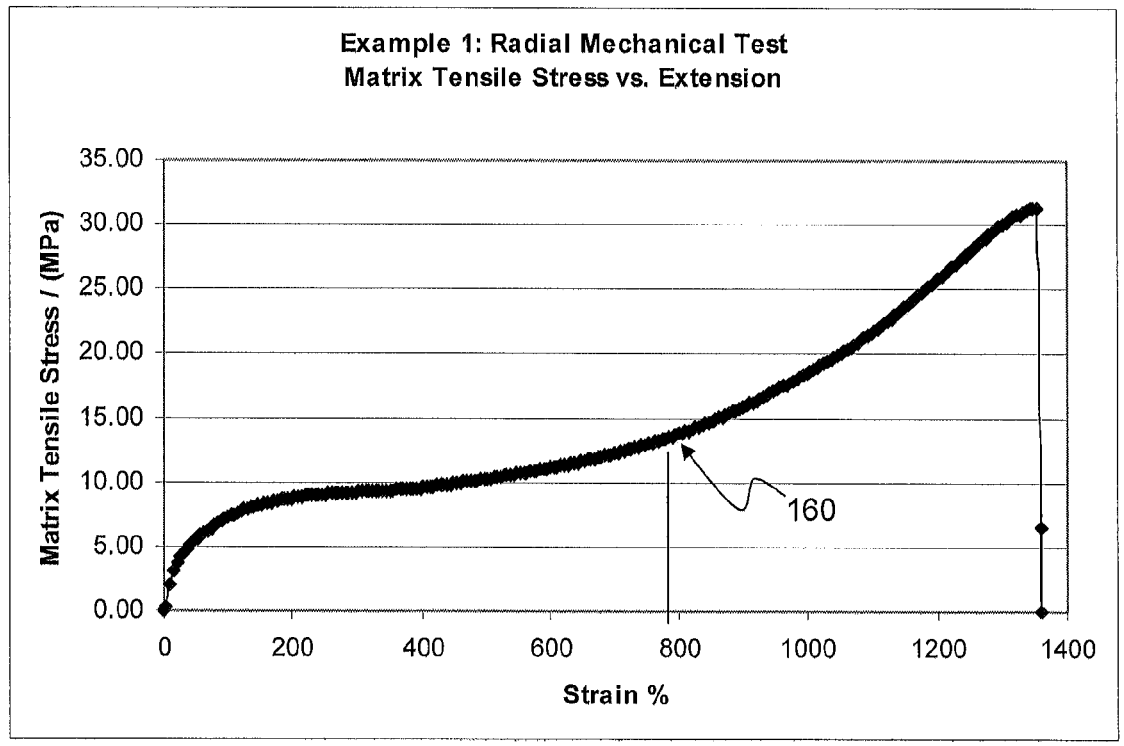
FIG. 17A shows a radial mechanical test response of example 1.
Figure 17B:
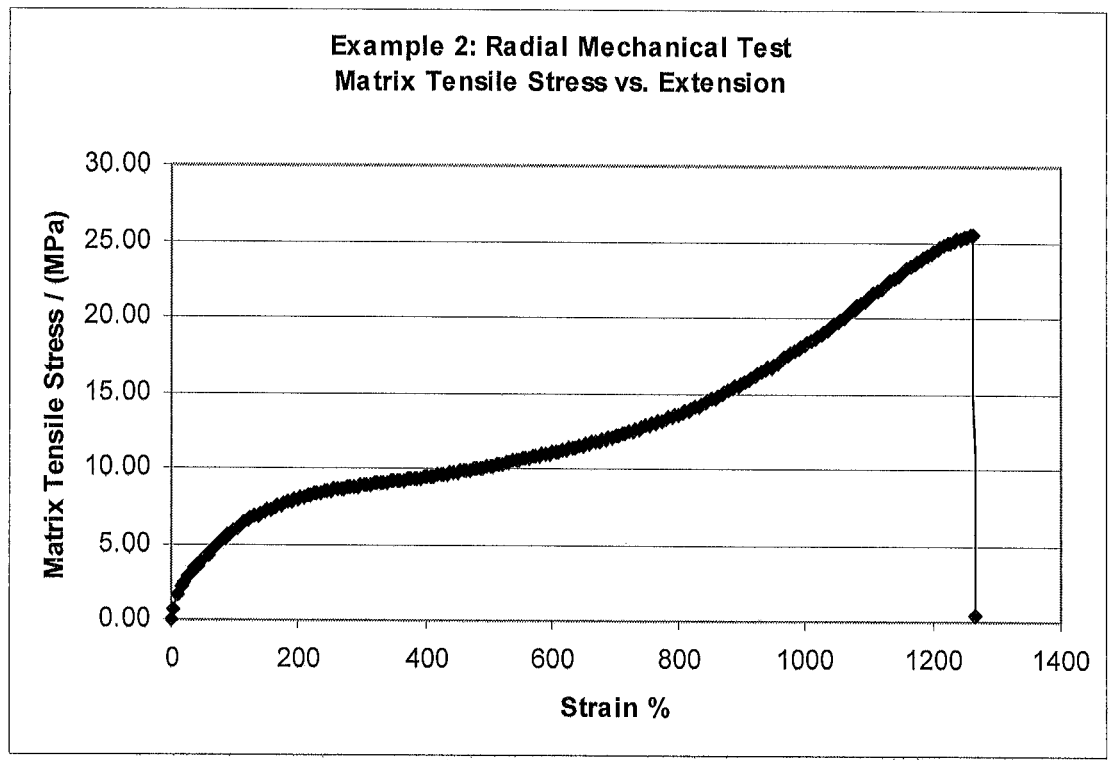
FIG. 17B shows a radial mechanical test response of example 2.
Figure 17C:
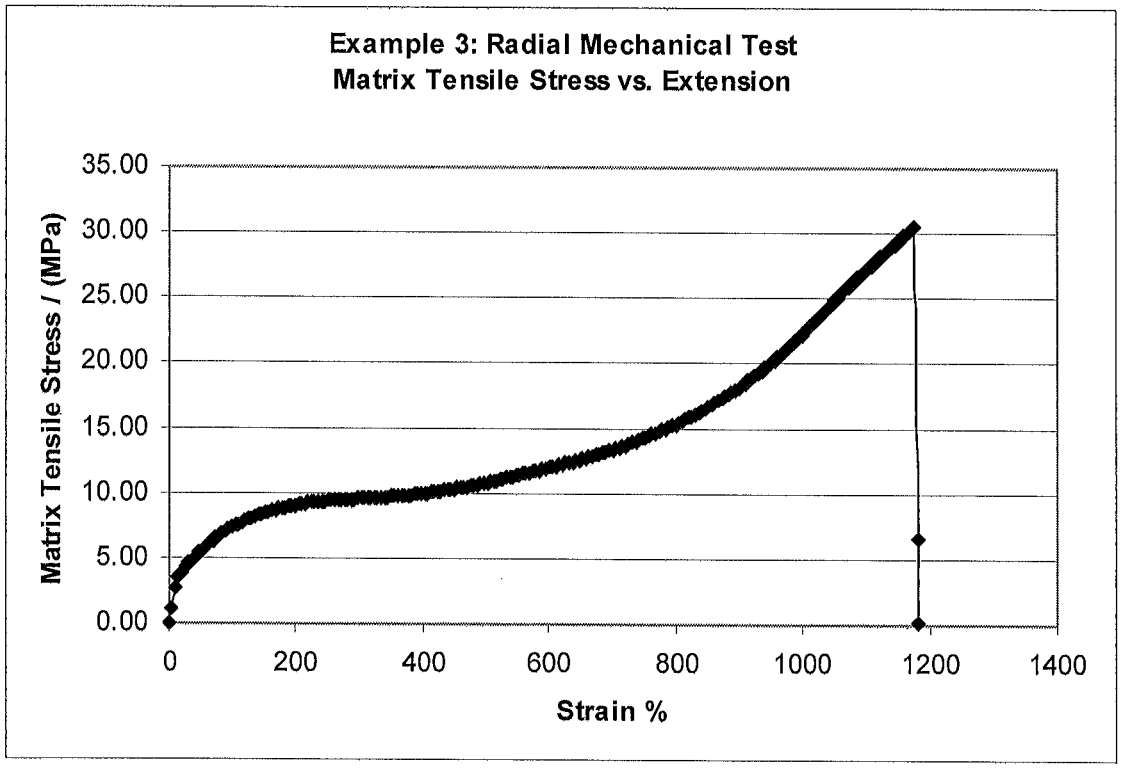
FIG. 17C shows a radial mechanical test response of example 3.
Figure 17D:
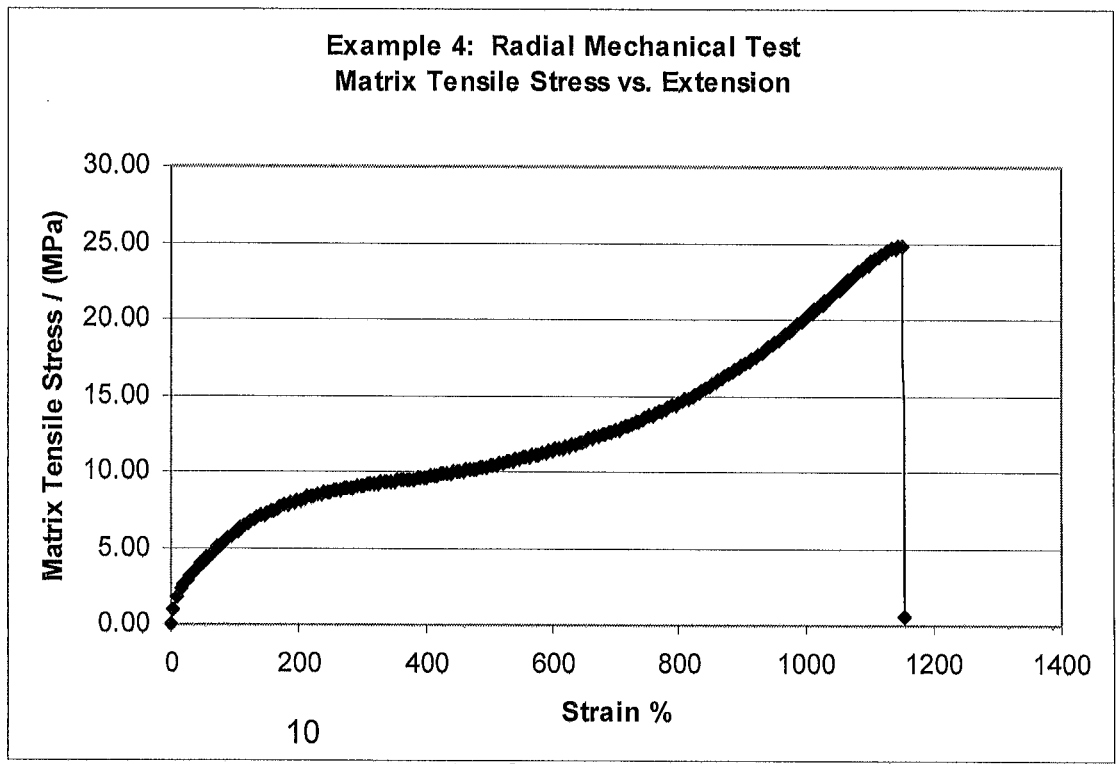
FIG. 17D shows a radial mechanical test response of example 4.

The band of expanded fluoropolymer may be distended manually in one embodiment to a desired extent. It was surprisingly discovered that the bands of the present invention could be extended to such a high degree as depicted in FIGS. 16 and 17A, where the band was distended to a strain of more than 1200% without breaking. In addition, the dramatic increase in strength of the band as it was distended to higher amounts of strain in the radial direction was surprising.

It is preferable that the force required to distend the band is sufficiently low, such that the band does not cause the user discomfort during the distention process. In some embodiments, as shown in FIG. 16 and FIG. 17A through 17D, the band of the present invention may be capable of being distended at least two times its original dimension, or to 100% strain, with a force of no more than 20N. Likewise, the expanded fluoropolymer band may exhibit a matrix tensile stress of no more than 10 MPa when distended in the radial direction 100% or less as described in the radial mechanical test herein. An important feature of the distensible band of the present invention is a low force or resistance for distention over a considerable amount of strain, coupled with a higher resistance at higher strain, thereby creating a limit or stop. This limit or stop may encourage or alert the user to stop distending the band and thereby prevent breaking the band. As is shown in FIG. 17A through 17D there is an inflection point 160 around 800% strain, where the matrix tensile stress of the band increases quickly, thereby providing the user with an indication to stop distending the band.

Figure 18:
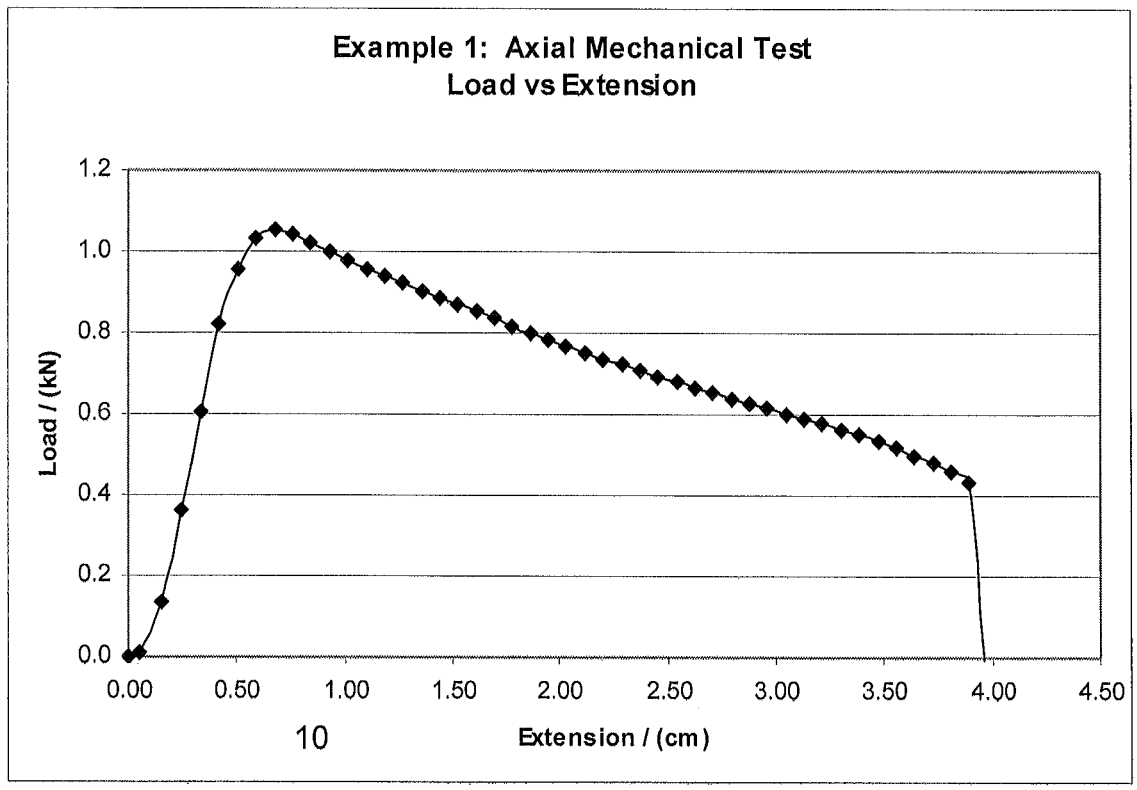
FIG. 18 shows an axial mechanical test response of example 1.

The axial strength of the distensible band in some embodiments is much greater than the strength in the radial direction as shown in FIGS. 18 and 19A through 19D. As shown in FIG. 18, the force required to distend the expanded fluoropolymer in the axial direction was more than 1 kN, and the maximum strain was less than 100%. Matrix tensile strength values of some embodiments of the present invention in both the axial and radial direction, as well as a ratio of the axial to radial matrix tensile strength are provided in Table 6. It has been found that a distensible band having a much higher axial matrix tensile strength than radial matrix tensile strength is preferred in some embodiments. The ratio of axial to radial matrix tensile strength may be high, such as greater than 5, 10, 15, or 20, or between 5 and 20, 10 and 20, or between 10 and 15. Bands having this high ratio of matrix tensile values have been found to be easily distensible but strong, abrasion resistant and durable in the distended or second stretched state.

The distensible band of the present invention in some embodiments changes dimensions dramatically as it is stretched from a first state to a second stretched state. In one embodiment the distensible band is stretched from a first state in which the band is unsuitable for use as a dental cleaning article to a second state, where it can be easily manipulated as a dental cleaning article. The diameter of the distensible band increases as the band is stretched and in some cases the width and/or thickness decrease. The width in a second state may be less than one quarter the width of the band in the first state. The cross sectional area of the band may be reduced to one quarter the cross sectional area of the band in the first state. The dimensional changes of some bands stretched to various strain levels is reported in Table 8A through 8C.

Expanded polymer and expanded fluoropolymer in many cases exhibits no or limited elastic properties. Therefore, in some embodiments, the distensible band of the present invention may not be elastic nor substantially dimensionally recoverable, as it does not exhibit any substantial dimensional recovery after stretching from a first state to a second stretched state. In particular, when the distensible band is comprised essentially of expanded fluoropolymer, the band is substantially dimensionally non-recoverable. In other embodiments however, an elastomeric material may be incorporated into or on the dental cleaning article and provide elastic, or dimensional recovery properties.

Figure 20A:
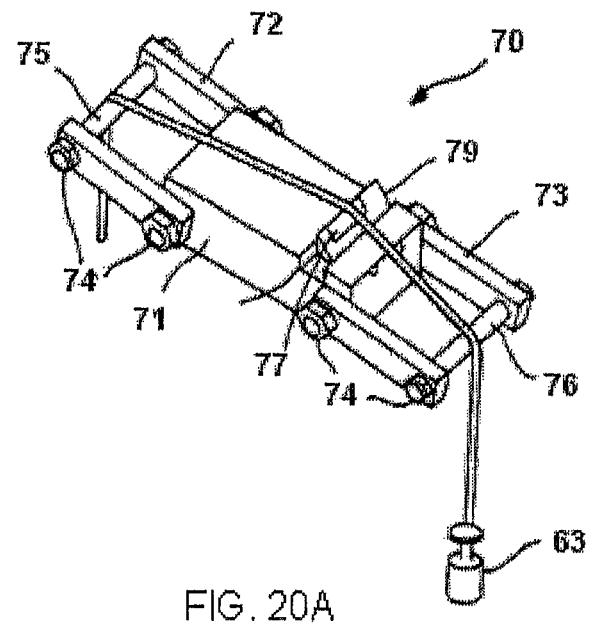
FIG. 20A shows an isometric view of the abrasion test apparatus.
Figure 20B:
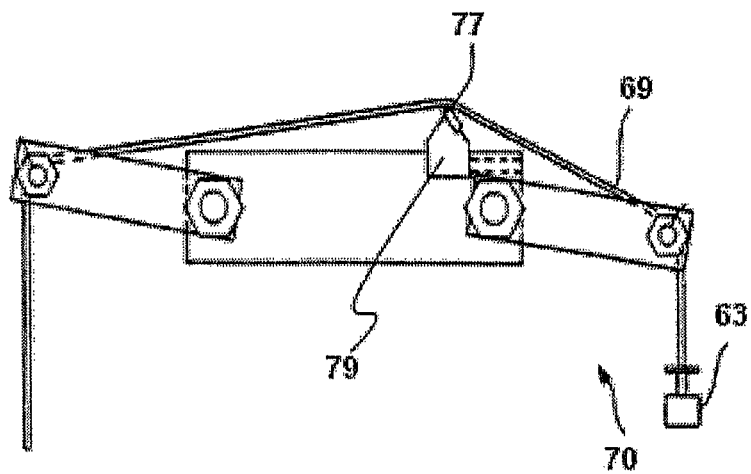
FIG. 20B shows an isometric view of the abrasion test apparatus.

An important attribute of dental cleaning articles such as dental floss, is abrasion resistance or abrasion durability. Dental cleaning articles are traversed across and between teeth which can be rough or have sharp edges that can abrade and cause the article to break prematurely. Some embodiments of the present invention have been found to be surprisingly abrasion resistant. Table 9 provides abrasion results of distended bands made according to the examples herein and tested according to the abrasion test described herein. The abrasion test is shown in FIGS. 20A and 20B.

Figure 21:
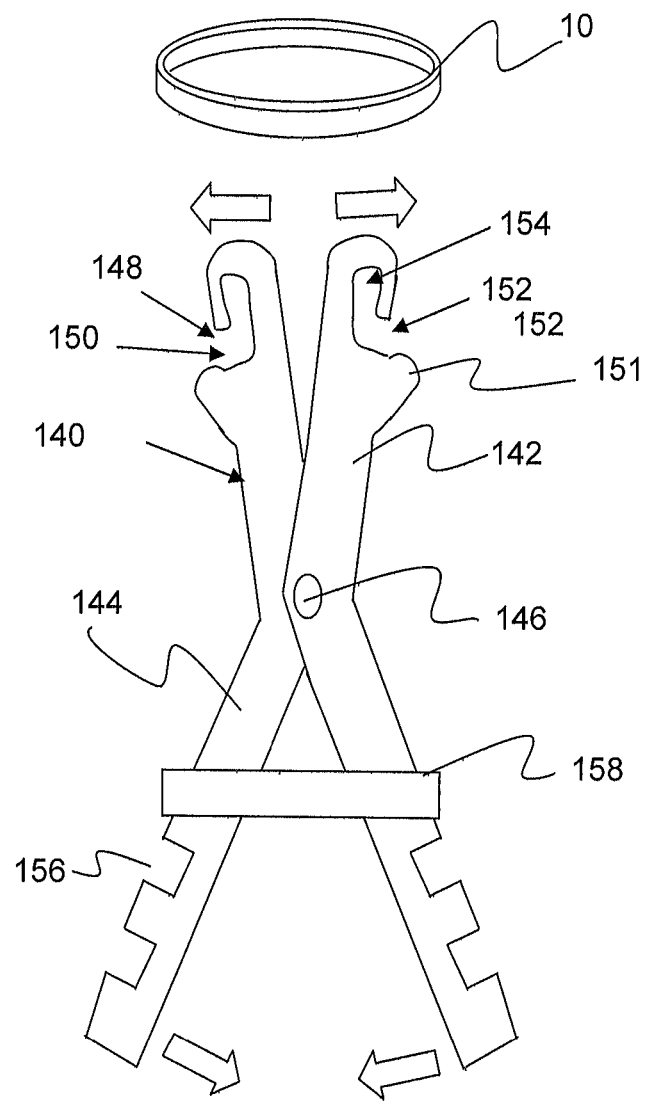
FIG. 21 shows a distensible band support device.

The dental cleaning article of the present invention can be used in any conventional way including manually, or as a floss pick, wherein the band is attached to a support. In another embodiment, the band is configured onto a support device that in one embodiment comprises a means to facilitate the distension of the band. In one embodiment, the support device comprises a first support member 142, a second support member 144, and a pivoting point 146, whereby the user can squeeze the support and distend the band, as is depicted in FIG. 21. The support device 140 may further comprise a band securing portion 148 such as a recess 150, or raised portion 151 along at least one support member, as depicted in FIG. 21. In a preferred embodiment, the band securing portion comprises a recess, and more preferably a recess having at a channel 154, or contour that extends beyond the largest dimension of the opening 152 along the support member 142, as depicted in FIG. 21. Other configurations of support members have been envisioned, whereby in some embodiments the user may pull or open the members thereby distending the band. In addition, the support member may further comprise an elastomer or spring that may facilitate the distension of the band, or keep the band in tension after distension. In an alternative embodiment, the support members further comprise a locking mechanism that allows the user to lock the support members in place relative to each other after distending the band. An example of a locking mechanism includes but is not limited to a notch and latch configuration as depicted in FIG. 21, where the latch 158, can be slid down the support members and secured by the notches 156 along the support member thereby temporarily locking the support members in position relative to each other.

Test Methods
Matrix Tensile Stress and Strength

Matrix tensile strength (MTS) is calculated using the following equation:

$$MTS = \left(\frac{Maximum\_Load}{Cross\_sectional\_area}\right) * \left(\frac{2.2}{\rho_0}\right)$$

where the cross-sectional area and density $\rho_0$ of the sample are measured prior to the tensile test. The cross-sectional area of the sample is measured using a standard snap gauge to measure the thickness of the sample, and the width of the sample is measured using a standard dial caliper. The cross-sectional area is the product of the width and thickness. The mass of the sample is measured using a mass balance having one-thousandth gram resolution and the length of the sample is measured using a standard dial caliper. Density $\rho_0$ is calculated by dividing the mass by the product of the length and cross-sectional area.

Figure 14:
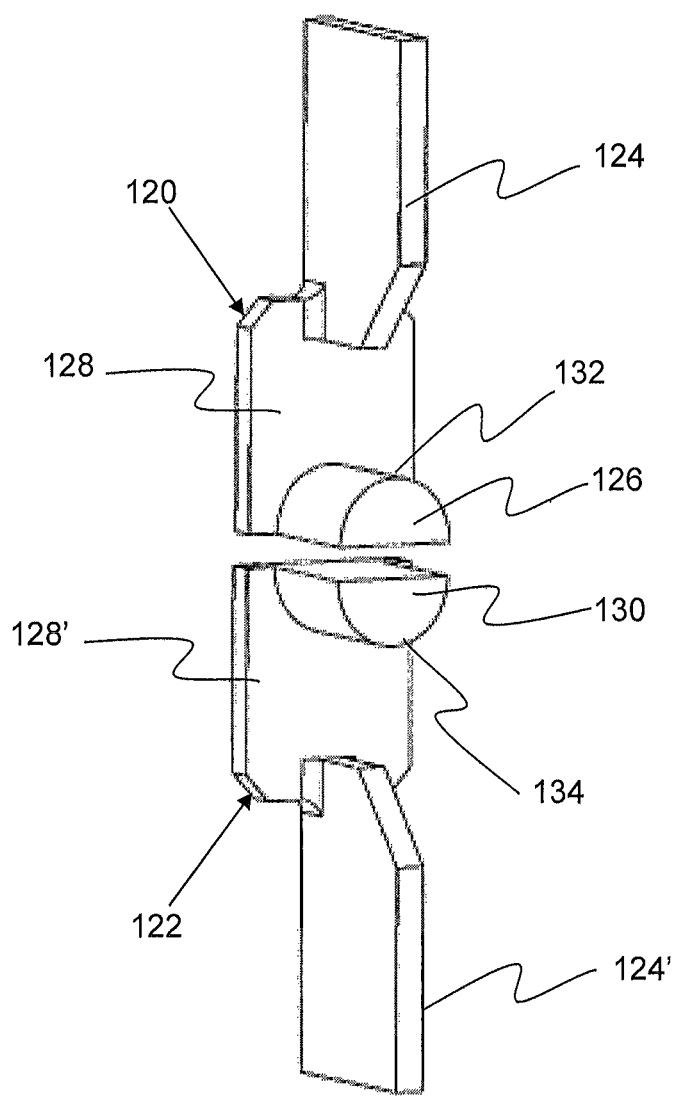
FIG. 14 shows an isometric representation of the radial test fixtures.
Figure 15:
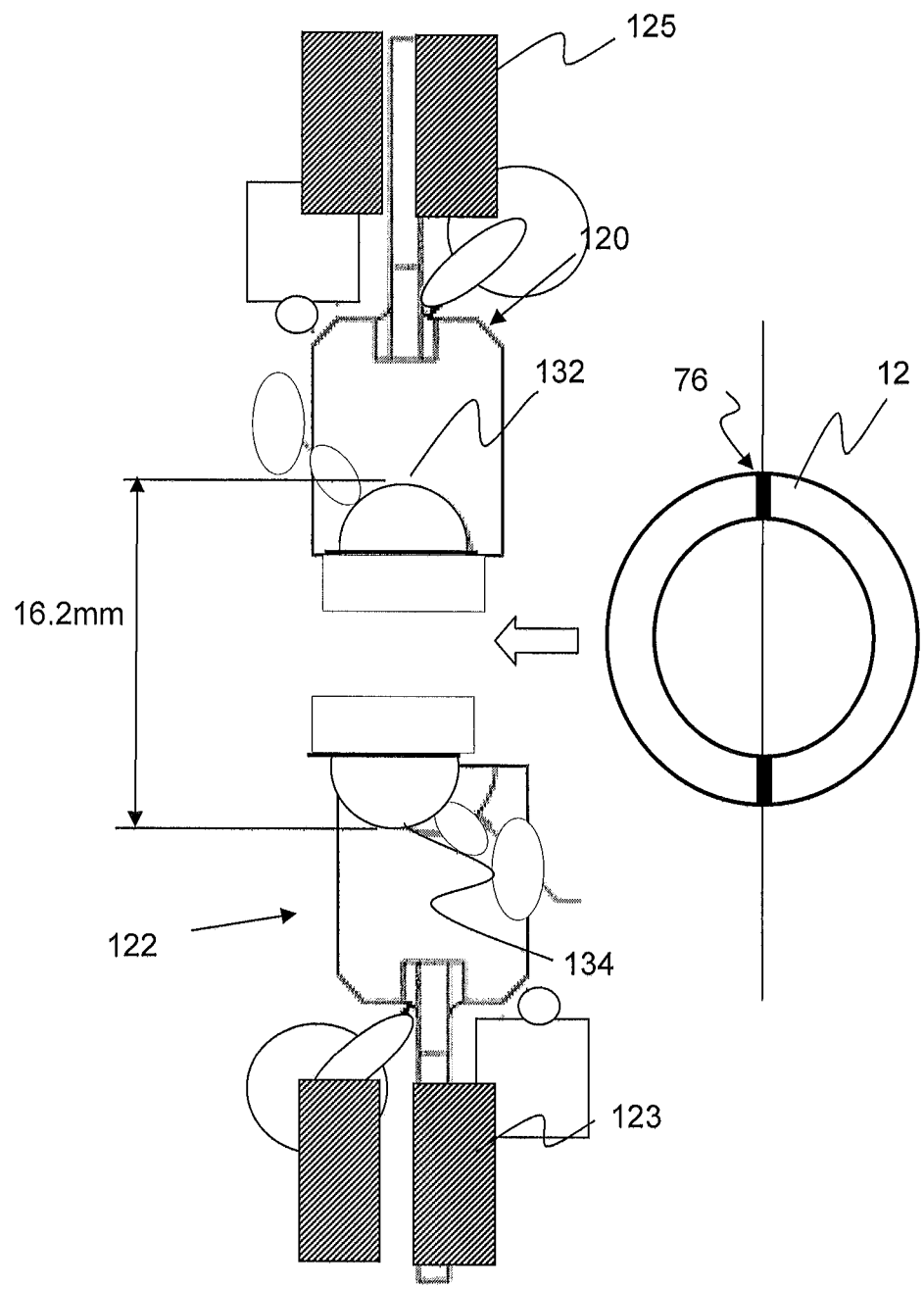
FIG. 15 shows a front view of the radial test fixtures and a distensible band.

The matrix tensile stress was calculated using the same method as the matrix tensile strength, except that the tensile load was used in place of the maximum load.
Band Radial Mechanical Test Method For the purposes of this invention, test fixtures 120, 122 were constructed to support the band during mechanical testing. The test fixtures depicted in FIG. 14 comprise a clamping plate 124, 124' and a curved support peg 126, 130. The semicircular shaped support pegs had a 6.35 mm diameter and extended from the support bracket 128, approximately 14.2 mm. The test fixtures were clamped into the top and bottom grips 125, 123 of the Instron, Model 5567 and a 16.2 mm gap was set between the top of the top support peg 132 and the bottom of the bottom support peg 134 as depicted in FIG. 15. A 6.35 mm wide band 12 cut from expanded fluoropolymer tubing was placed around the fixture directly in line and centered under the load cell to minimize moment generation. The top test fixture 120 was then pulled at a rate of 50.8 cm/min until the cut band of expanded tubing fractured or broke. The load and displacement were recorded. The engineering stress, matrix tensile stress, and matrix tensile strength were calculated using the initial dimensions of the band, including width, thickness, mass, and a density of PTFE of 2.2 g/cc. Matrix tensile stress values were calculated by multiplying the engineering stress by the ratio of the density of PTFE to the density of the sample.

Axial Mechanical Test Method

A 15.24 cm long sample of tubing was clamped into the grips of an Instron, Model 5567 with the length of the tubing substantially parallel with the direction of testing. The gauge length between the grips was 5.08 cm and the rate of pull was 50.8 cm/min. The load and displacement was recorded. The engineering stress, matrix tensile stress, and matrix tensile strength were calculated using the initial dimensions of the material, including width, thickness, length, mass, and a density of PTFE of 2.2 g/cc. Matrix tensile stress and strength values were calculated by multiplying the engineering stress by the ratio of the density of PTFE to the density of the sample.

Interval Stain Test Method

A tensile tester, Instron Machine, Model 5567 outfitted with a pair of standard pneumatic actuator grips dimensioned 2.54 cm by 2.54 cm flat grips was use to strain samples to discrete intervals. Three specimens per sample were tested to each of the displacements. A 6.35 mm wide tube section was cut across the width and placed in the Instron with the long axis, or radial direction in alignment with the pulling direction. To minimize moment generation about the specimen during testing, specimens were oriented in the Instron grips such that they were directly in line and centered under the load cell. The gauge length was 25.4 mm, and the cross head speed was 50.8 cm per minute. The test was completed when the specimen was extended to the desired percent strain, (100%=25.4 mm cross-head displacement, 400%=76.2 mm cross-head displacement and 800%=177.8 mm cross-head displacement). The load and displacement were recorded. The matrix tensile stress at each interval of strain was calculated and reported.

Sheet Band Mechanical Test Method

A 2.54 cm outer diameter by 1.95 cm inner diameter doughnut shaped article was stamped out of sheets of expanded fluoropolymer. The machine direction was marked on the sample for orientation on the test fixture. Five samples of the sheet band were tested in the machine direction and five samples were tested in the cross-machine direction. When testing the machine direction, the mark 76 indicating the machine direction was aligned in the direction of the pull as shown in FIG. 15. When testing the cross machine or cross machine direction the mark was oriented perpendicular to the direction of the pull.

Sheet Material Mechanical Test Method

The machine and cross machine matrix tensile stress of sheet material was determined using an Instron Machine, Model 5567. The gauge length was set to 25.4 mm, and the samples were pulled at a rate of 50.8 cm/minute. Three 6.35 mm wide cm by at least 5 cm long samples were cut from the sheet material with the longer dimension in the machine direction, and three were cut with the longer dimension in the cross machine direction. A sample of sheet material was placed in the 2.54×2.54 cm square knurled surface grips of the Instron with the longer dimension aligned with the direction of pull. The matrix tensile strength was calculated as described herein.

Abrasion Test Method

The distended bands of expanded fluoropolymer produced according to this invention were tested for abrasion resistance. The bands were distended and then cut to form a strand of floss for mounting in the abrasion resistance device 70 as shown in FIGS. 20A and 20B. The device 70 has a base 71 made of stainless steel. Extension assemblies 72 and 73 project from the base 71 and are adjustably attached thereto by bolts 74. Each extension assembly 72 and 73 has a roller 75, 76 attached thereto by bolts 74. A micro grain carbide blade 77, part number AL-8 available from Micro-IOO, Inc. Los Angles, Calif., is supported on support 79. The blade 77 was wiped with a micro-wipe towel saturated with a 90% solution of IPA and deionized water and wiped with a clean and dry cotton towel prior to each test.

As shown in FIG. 20A, a sample of floss 69 was laid over the device 70 such that floss contacts the device at three points: at roller 75, blade 77, and roller 76. The angle of extension assemblies 72 and 73 was set so that floss 69 was as close as possible to base 71 without actually touching the base. One end of floss 69 was attached to a 289 gram mass 63 and the other end of floss was attached to a reciprocating linear actuator (not shown) that repeatedly pulled floss 69 over device 60. The reciprocating linear actuator had a stroke length of 20.6 mm and a rate of 54 strokes per minute (each stroke is one back-and-forth cycle). The floss was cycled until failure. The number of cycles was recorded and is reported in Table 9. The floss was removed from the testing device and the blade 77 was wiped with a micro-wipe towel saturated with a 90% solution of IPA and deionized water and wiped with a clean and dry cotton towel.

DEFINITIONS

Dental cleaning article as used herein is defined as a band of material for cleaning between teeth.

Distensible band as used herein refers to the dental cleaning article of the present invention in the first state.

Tube section as used herein is defined as a section formed from a tube, as for example, through cutting across the length of the tube, to form a band.

Sheet band as used herein is defined as a material having a central opening and in one embodiment is formed from a sheet or sheets of material.

High density region as used herein is defined as a region along the band that has a density greater than an adjacent region. In one embodiment the density of the high density region is at least twice the density of an adjacent region.

Low density region as used herein is defined as a region along the band that has a density lower than an adjacent region. In one embodiment the density of the low density region is at least one half the density of an adjacent region.

Force to break of the distensible band as used herein is defined as the maximum load measured when tested according to the Band Radial Mechanical Test Method described herein.

Matrix tensile strength ratio as used herein is the ratio of the matrix tensile strength of the distensible band in two orthogonal directions, such as axial and radial, or longitudinal and cross machine directions.

Radial matrix tensile strength as used herein is defined as the matrix tensile strength measured according to the Radial Test Method described herein.

Stretched as used herein, in reference to stretching the distensible band from a first state to a second stretched state, is performed at room temperature conditions.

Room temperature as used herein means the temperature at which people are accustom while indoors, and is usually approximately 20° C.

Example 1

Bands of dental floss of the present invention were made by extruding and expanding a tube of PTFE and cutting the tube into bands. Mineral spirit ISOPAR® K from the EXXON Company was blended with a fine powder PTFE from the DuPont De Nemours Company (Wilmington, Del.) at a ratio of 0.217 g/g of resin. The mixture was permitted to rest for a period of 24 hours at a temperature of 30° C. Following the resting period, the mixture was placed into and compressed inside an extruder having an inner diameter of approximately 116.8 mm. The compressed mixture was extruded through a die and tip arrangement, heated to approximately 30° C., at a reduction ratio of approximately 350:1, to produce an extruded tube having an approximately 23.9 mm outer diameter and an approximately 0.406 mm wall thickness.

The extruded tubing was then heated, expanded and sintered to produce an expanded fluoropolymer tube having nodes interconnected by fibrils. The extruded tubing was preheated in a forced air oven, set to a temperature of 415° C., and expanded at a ratio of 4.3:1 in an oven set to a temperature of approximately 355° C. The tubing was then sintered while held in tension at a temperature of approximately 445° C. for approximately 12 seconds. The take up speed of the tubing from this process was approximately 3.0 m/min. This process produced an expanded fluoropolymer tube having the properties listed in Table 2.

Figure 19A:
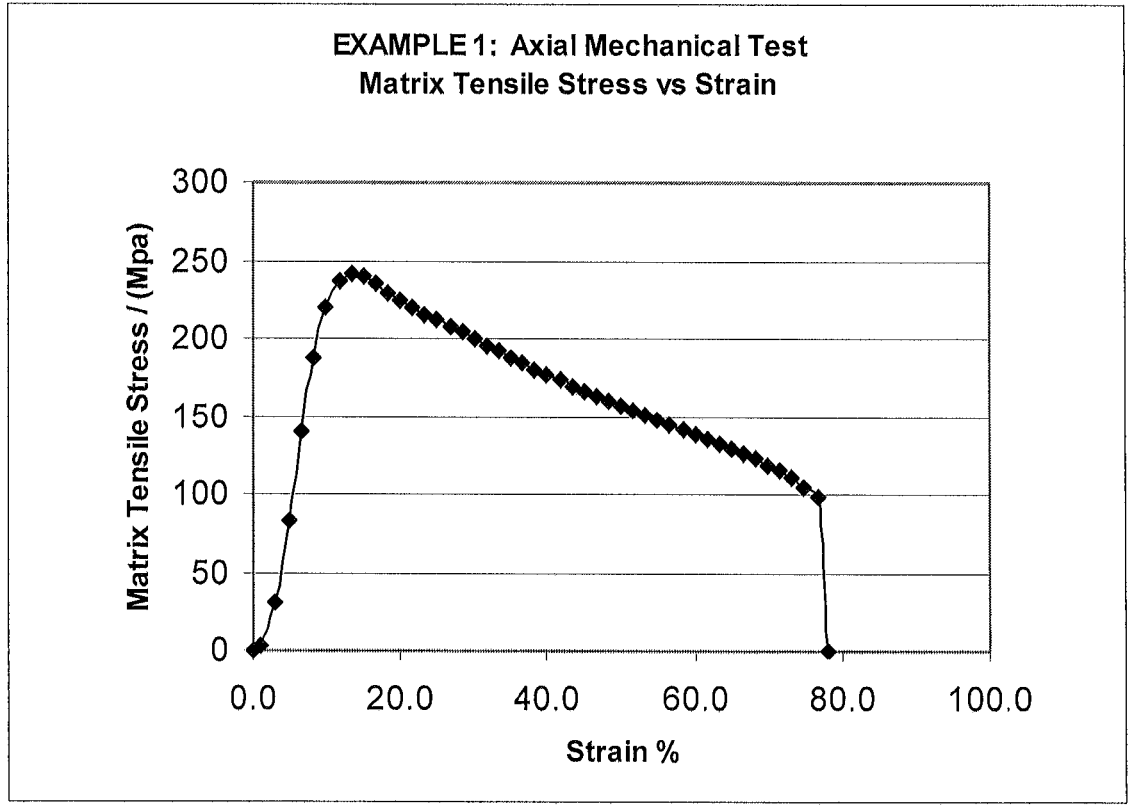
FIG. 19A shows an axial mechanical test response of example 1.

The expanded tubing was cut into 15.24 cm lengths and tested according to the Axial Mechanical Testing Protocol described herein, and the results are reported in Table 5 and FIGS. 18 and 19A. In addition, approximately 6.35 mm wide bands were cut from the expanded tubing and tested according to the Radial Mechanical Testing Protocol described herein, and the results are reported in Table 3 and 4, and FIGS. 16 and 17A. An SEM of this expanded tubing before and after radial mechanical testing is shown in FIGS. 2A and 2B respectively.

As can be seen in FIG. 16, the force to distend the band in the radial direction is initially relatively low, and then as the band is distended further, the force becomes increasingly higher until the band breaks. It is desirable for the band of expanded fluoropolymer to be capable of being distended manually, and that the force required to distend the band will not cause discomfort, for example where the band rests on the fingers. The force required to strain the band of example 1 in the radial direction 800% was approximately 17N or less.

FIG. 17A shows the matrix tensile stress versus strain for the band of expanded fluoropolymer tested under the radial mechanical test protocol. The matrix tensile stress required to distend the band to 200% and even 400% strain is less than 10 MPa.

Example 2

An expanded fluoropolymer tube was created according to the process described in Example 1 except that the expansion ratio was 6.2:1, as described in Table 1. This process produced an expanded fluoropolymer tube having the properties listed in Table 2.

Figure 2C:
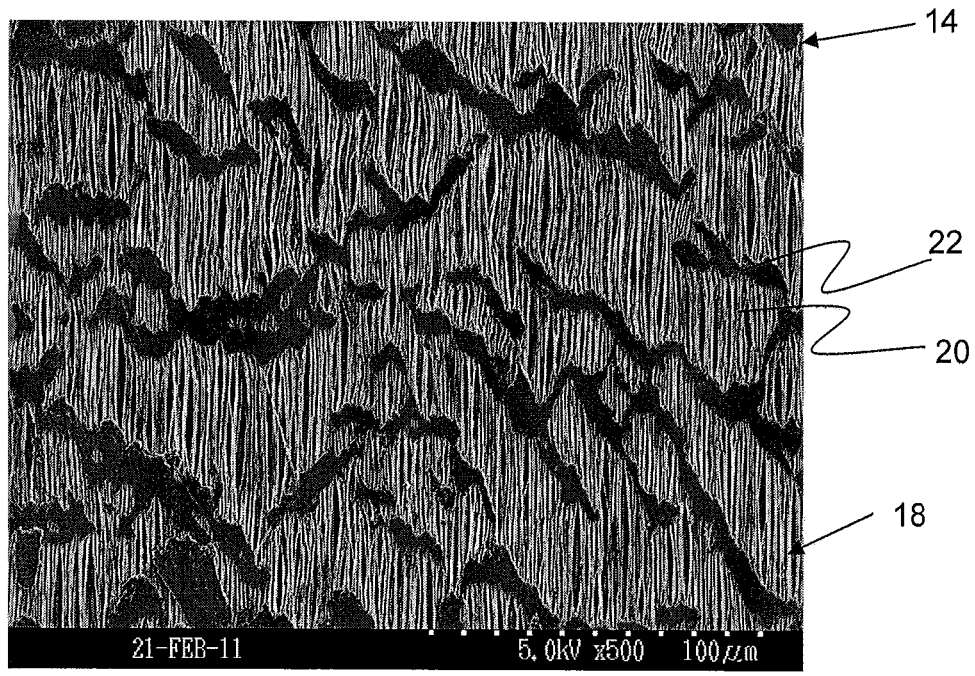
Figure 2D:
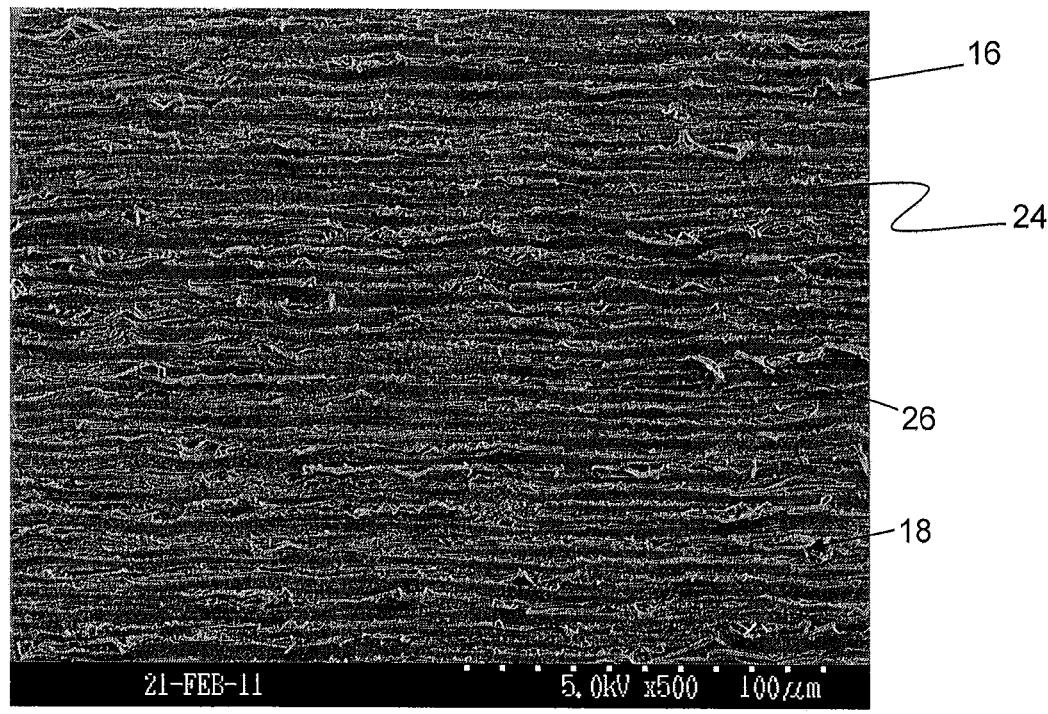
Figure 19B:
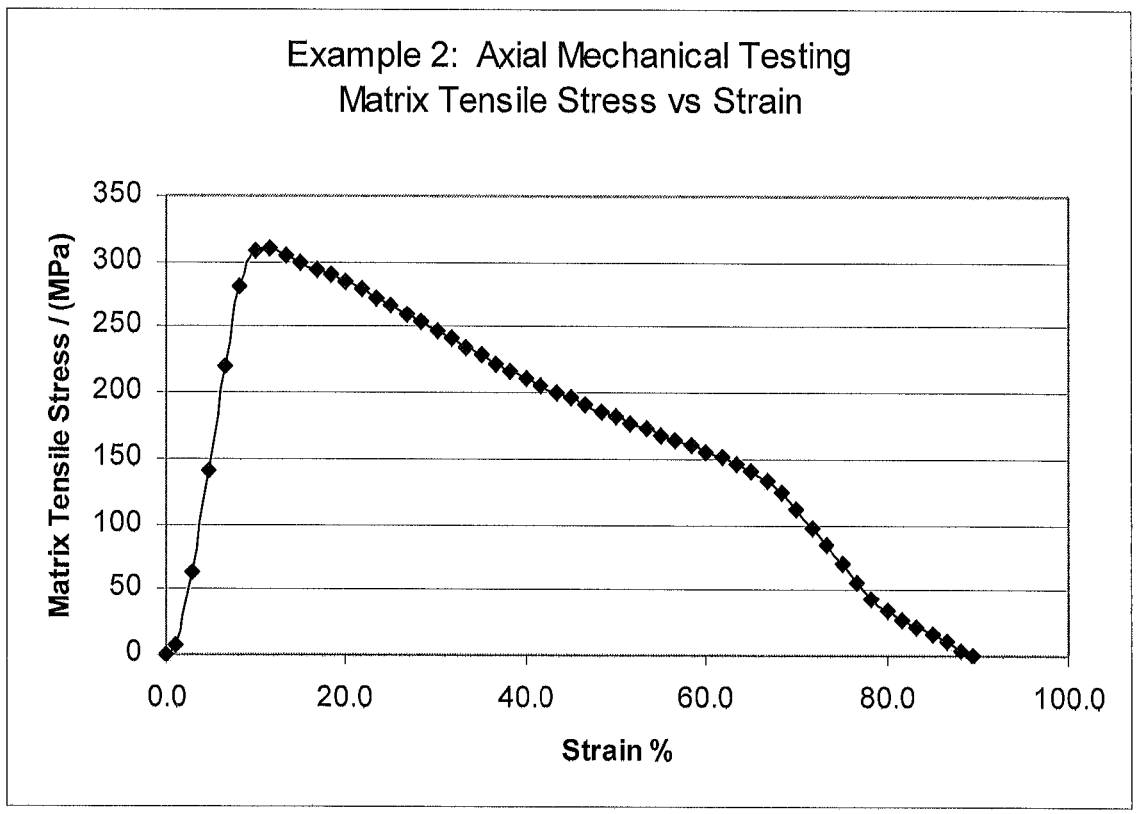
FIG. 19B shows an axial mechanical test response of example 2.

The expanded tubing was cut into 15.24 cm lengths and tested according to the Axial Mechanical Testing Protocol described herein, and the results are reported in Table 5 and FIG. 19B. In addition, approximately 6.35 mm wide bands were cut from the expanded tubing and tested according to the Radial Mechanical Testing Protocol described herein, and the results are reported in Table 3 and 4, and FIG. and 17B. An SEM of this expanded tubing before and after radial mechanical testing is shown in FIGS. 2C and 2D respectively.

Example 3

An expanded fluoropolymer tube was created according to process described in Example 1 except that the expansion ratio was 4.2:1, the duration of sintering was approximately 20 seconds, and the take up speed was 1.8 m/min as described in Table 1. This process produced an expanded fluoropolymer tube having the properties listed in Table 2.

Figure 2E:
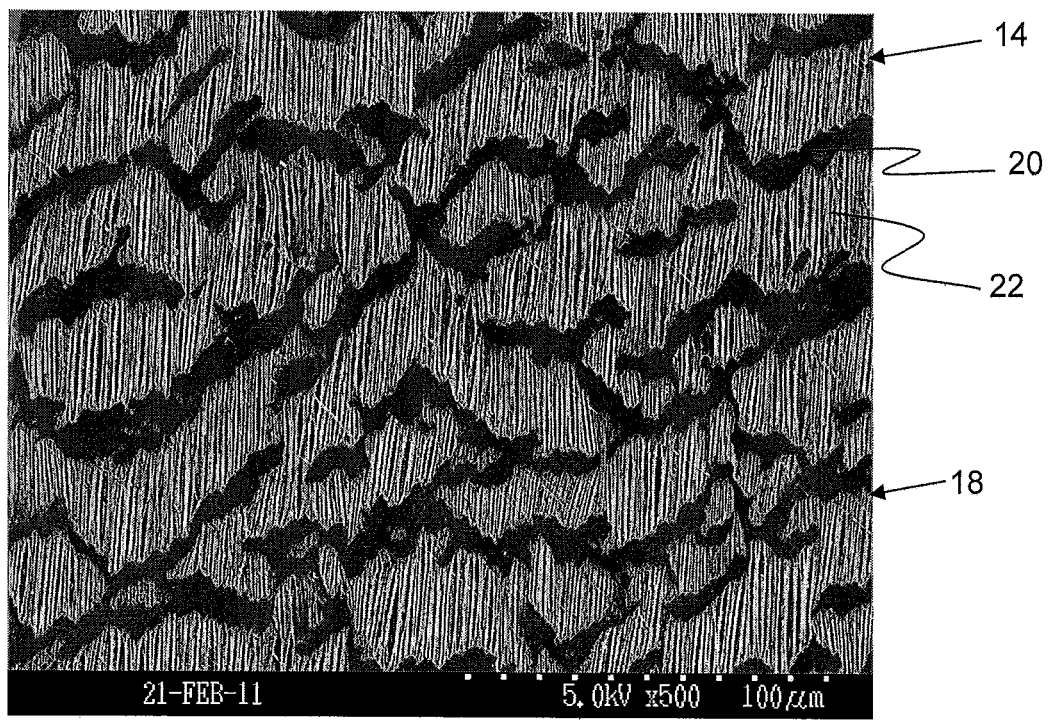
Figure 2F:
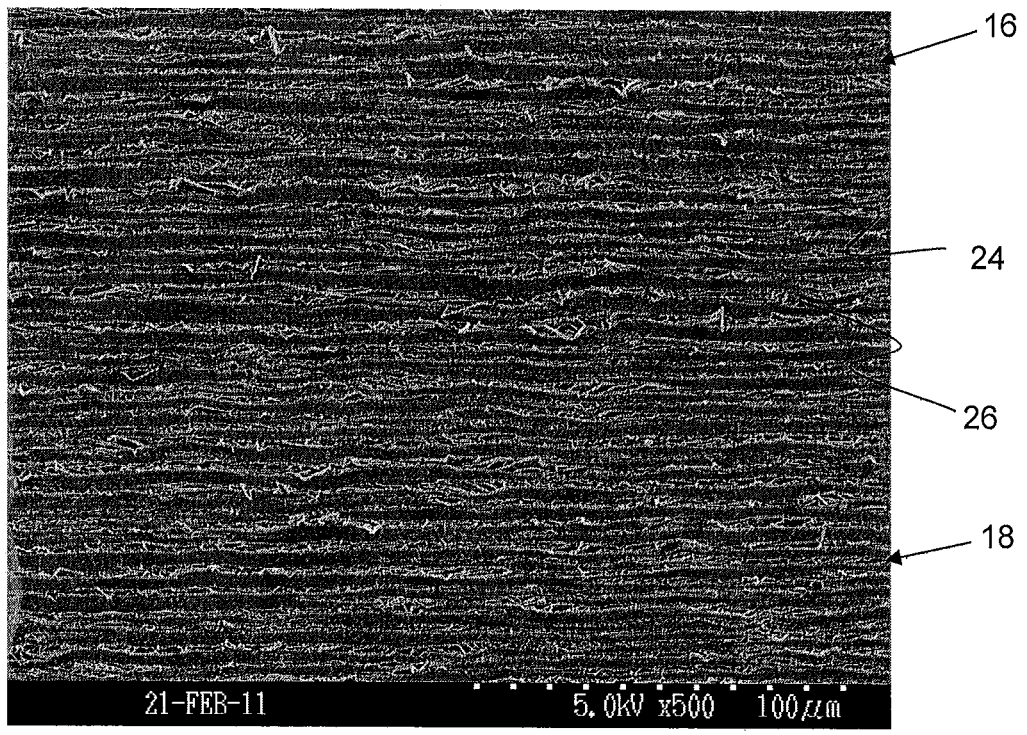
Figure 19C:
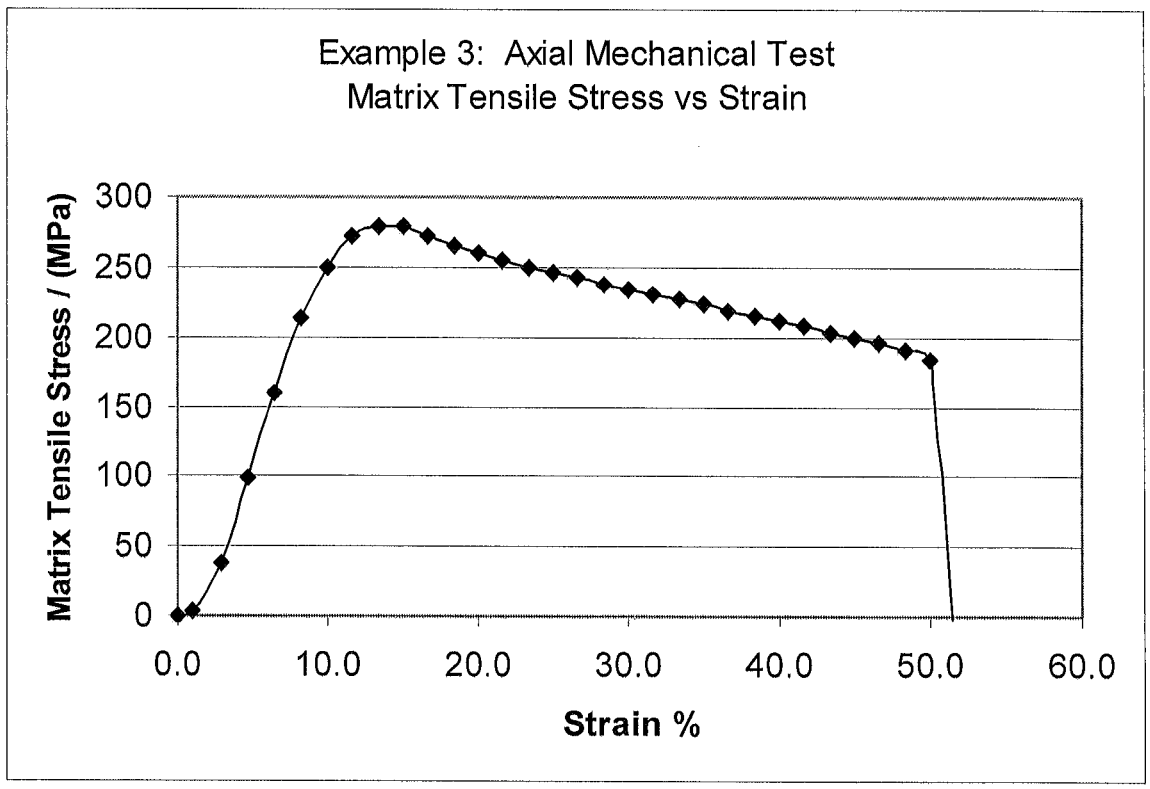
FIG. 19C shows an axial mechanical test response of example 3.

The expanded tubing was cut into 15.24 cm lengths and tested according to the Axial Mechanical Testing Protocol described herein, and the results are reported in Table 5 and FIG. 19C. In addition, approximately 6.35 mm wide bands were cut from the expanded tubing and tested according to the Radial Mechanical Testing Protocol described herein, and the results are reported in Table 3 and 4, and FIG. 17C. An SEM of this expanded tubing before and after radial mechanical testing is shown in FIGS. 2E and 2F respectively.

Example 4

An expanded fluoropolymer tube was created according to the process described in Example 1 except that the expansion ration was 6.1:1, the duration of sintering was approximately 20 seconds, and the take up speed was approximately 1.8 m/min as described in Table 1. This process produced an expanded fluoropolymer tube having the properties listed in Table 2.

Figure 2G:
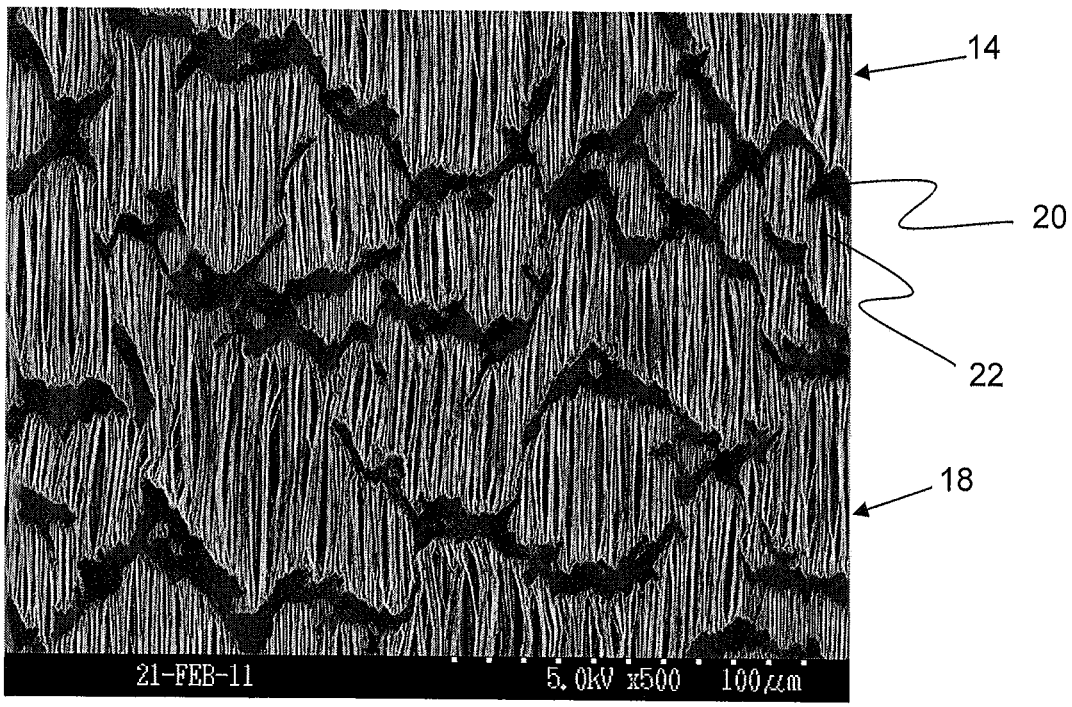
Figure 2H:
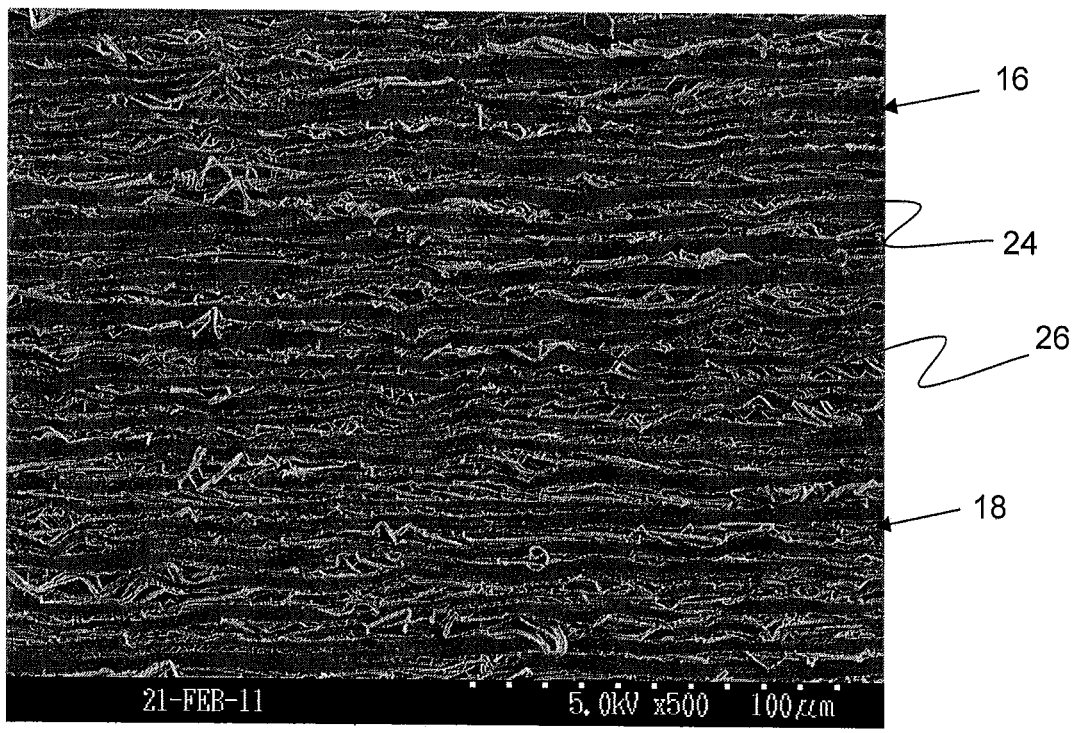
Figure 19D:
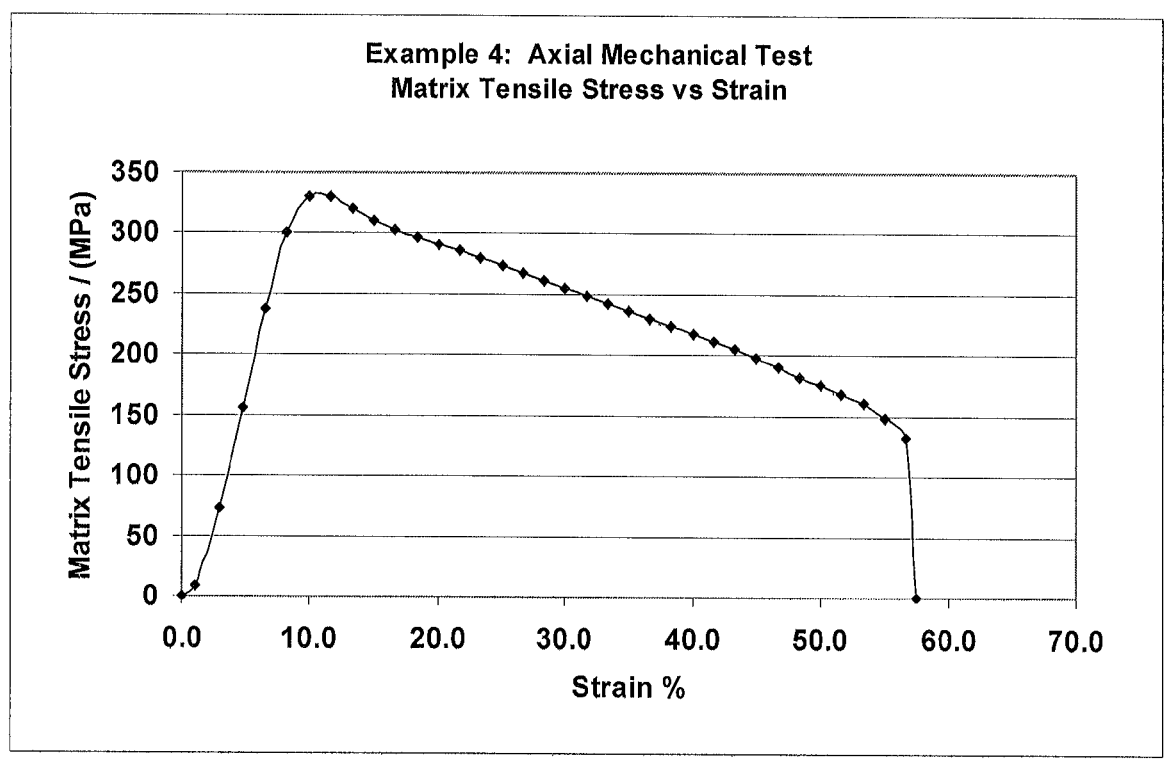
FIG. 19O shows an axial mechanical test response of example 4.

The expanded tubing was cut into 15.24 cm lengths and tested according to the Axial Mechanical Testing Protocol described herein, and the results are reported in Table 5 and FIG. 19D. In addition, approximately 6.35 mm wide bands were cut from the expanded tubing and tested according to the Radial Mechanical Testing Protocol described herein, and the results are reported in Table 3 and 4, and FIG. 17D. An SEM of this expanded tubing before and after radial mechanical testing is shown in FIGS. 2G and 2H respectively.

Example 5

A band of dental floss of the present invention was made by extruding and expanding a tube of PTFE and cutting the tube into bands. Mineral spirit ISOPAR® K from the EXXON Company was blended with a fine powder PTFE from the DuPont De Numerous Company (Wilmington, Del.) at a ratio of 0.217 g/g of resin. The mixture was permitted to rest for a period of 24 hours at a temperature of 30° C. Following the resting period, the mixture was placed into and compressed inside an extruder having an inner diameter of approximately 116.8 mm. The compressed mixture was extruded through a die and tip arrangement, heated to approximately 40° C., at a reduction ratio of approximately 752:1, to produce an extruded tube having an approximately 15.8 mm outer diameter and approximately 0.23 mm wall thickness.

The extruded tubing was then heated, expanded and sintered according to the process of Example 1, with the following exceptions, the expansion ratio was 4.3:1; the duration of sintering was approximately 5 seconds; and the take up speed was approximately 7.3 m/min (24 ft/min). This process produced an expanded fluoropolymer tube having the properties listed in Table 2.

Figure 2I:
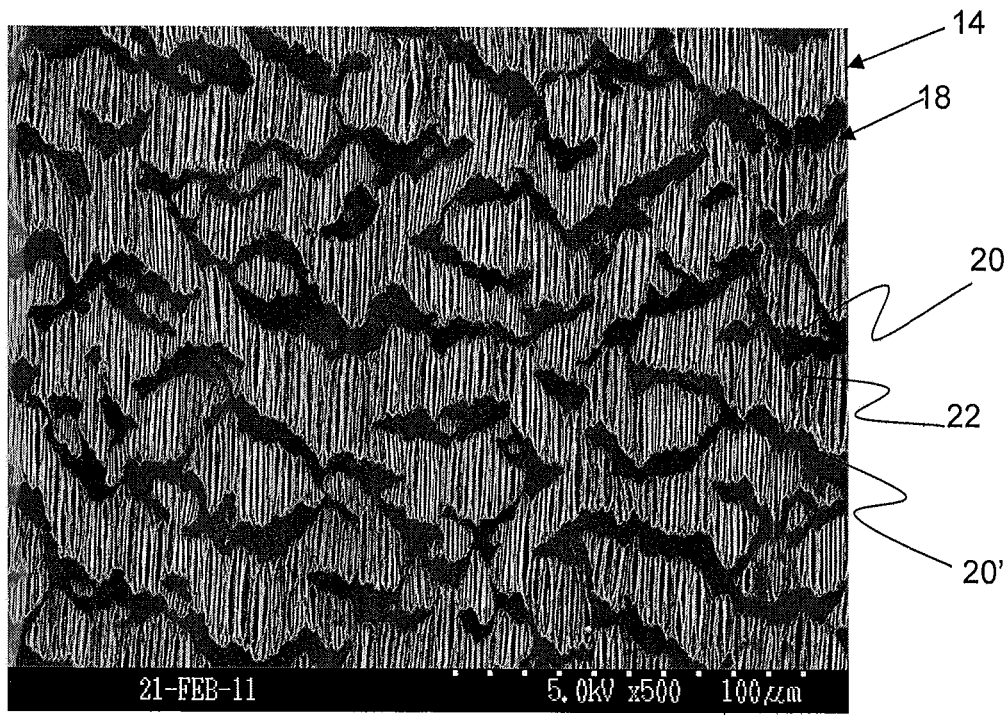
Figure 2J:
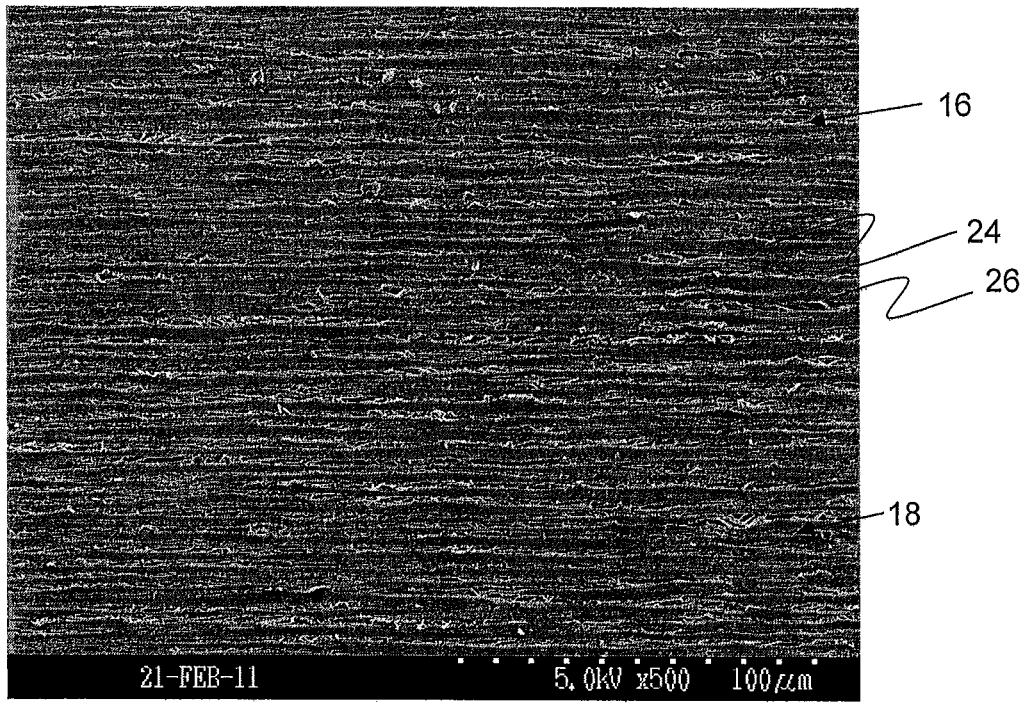

The expanded tubing was cut into approximately 6.35 mm wide bands and tested according to the Radial Mechanical Testing Protocol described herein, and the results are reported in Table 3 and 4. An SEM of this expanded tubing before and after radial mechanical testing is shown in FIGS. 2I and 2J respectively.

Example 6

Three approximately 0.95 cm wide sections of the floss band made according to Example 5 were stretched with a Shimpo Model FGE-100X digital force gauge, available from Electromatic Equipment Co., Inc. (Cedarhurst, N.Y.), in one hand and the index finger on the other hand. Force to stretch to a comfortable size without breaking was 24N, 25N, and 26N. The floss bands were each removed from the force gauge after stretching and used as dental floss.

Example 7

A sheet band was cut from a sheet of expanded PTFE membrane having a thickness of approximately 0.173 mm, and a density of approximately 0.95 g/cc. Fine powder of PTFE polymer as described and taught in U.S. Pat. No. 6,541,589 was blended with Isopar K (Exxon Mobil Corp., Fairfax, Va.) in the proportion of 0.201 g/g of fine powder. The lubricated powder was compressed in a cylinder to form a pellet and placed into an oven set at 70° C. for approximately 12 hours. Compressed and heated pellets were ram extruded to produce tapes approximately 15.2 cm wide by 0.508 mm thick. Two separate rolls of extruded tape were produced and layered together between compression rolls, and calendared down to thickness of 0.508 mm. The tape was then transversely stretched to approximately 55 cm (i.e., at a ratio of 2.8:1), and then dried in an oven set to approximately 250° C. while being restrained in the machine or longitudinal direction. The width after drying was approximately 33.7 cm. The dry tape was then longitudinally expanded between banks of rolls over a heated plate set to a temperature of 300° C. The speed ratio between the second bank of rolls and the first bank of rolls, and hence the expansion ratio, was 10:1. The approximately 8.9 cm wide longitudinally expanded tape was then restrained longitudinally and sintered at a temperature of approximately 365° C. for approximately 5 minutes. The process produced a thin strong porous expanded fluoropolymer sheet.

The sheet of expanded fluoropolymer was tested for longitudinal and transverse matrix tensile strength, by cutting 0.635 cm wide sample strips from the sheet in both the machine and cross-machine directions. The cut sections of material were oriented in the Instron with the long axis parallel to the direction of pull, and the sample was pulled at a rate of 50.8 cm/min. The gauge length was 2.54 cm. Three tests were performed in both the longitudinal and cross machine directions. The average machine and cross machine direction matrix tensile strengths were 180 MPa, and 7.5 MPa respectively. The ratio of the machine to cross machine strength was approximately 24. This is a very high ratio of strength in two orthogonal directions, much like the axial to radial matrix tensile strength ratios reported for the tubing made according to examples 1 through 4.

Figure 17E:
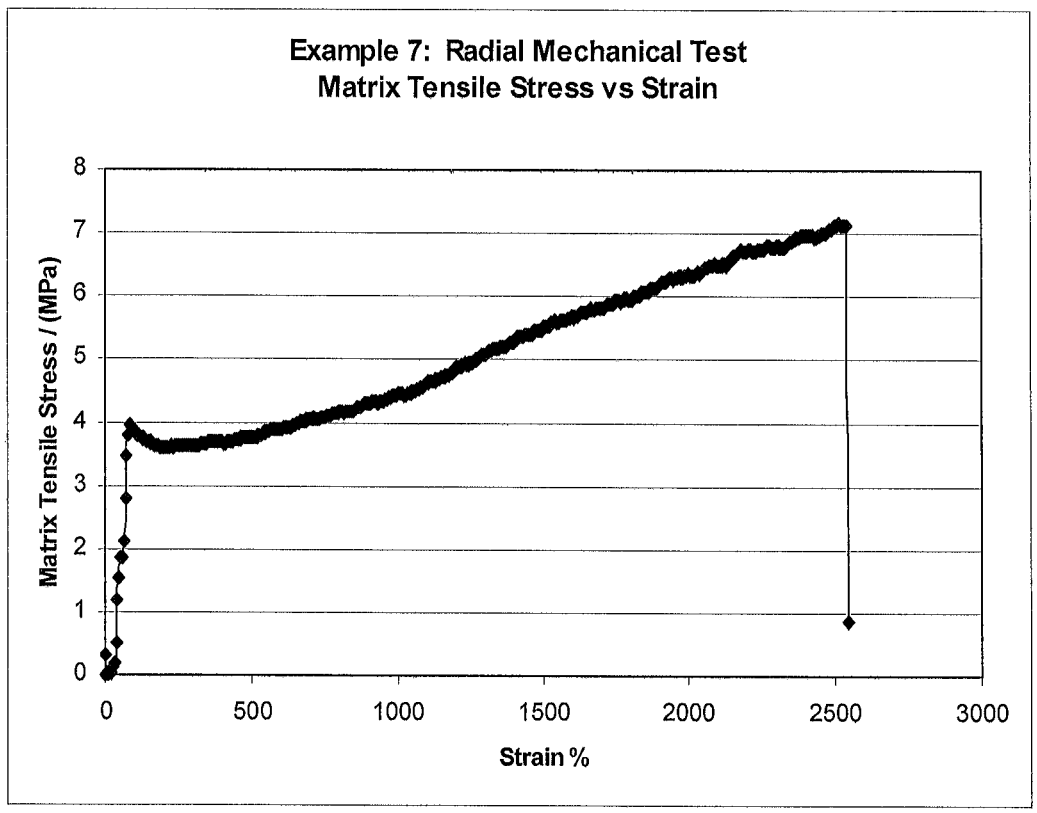
FIG. 17E shows the radial mechanical test response of example 7.

Ring shaped sheet bands were die cut from the sheet of expanded PTFE, having a 2.54 cm outer diameter by 1.95 cm inner diameter. The results of the Sheet Band Mechanical Testing Procedure are reported in FIG. 17E. In addition, the orientation of the sample during this test did not have a significant influence on the results.

TABLE 1

Expanded Fluoropolymer Tube Process Conditions

| Example Number | Expansion Ratio | Approx. Sintering Time (sec) | Output Speed (m/min) |
|---|---|---|---|
| 1 | 4.3:1 | 12 | 3.0 |
| 2 | 6.2:1 | 12 | 3.0 |

TABLE 1-continued

Expanded Fluoropolymer Tube Process Conditions

| Example Number | Expansion Ratio | Approx. Sintering Time (sec) | Output Speed (m/min) |
|---|---|---|---|
| 3 | 4.2:1 | 20 | 1.8 |
| 4 | 6.1:1 | 20 | 1.8 |
| 5 | 4.3:1 | 5 | 7.3 |

Table 1 provides a summary of some of the processing conditions used to make expanded fluoropolymer tubes.

TABLE 2

Expanded Fluoropolymer Tube Properties

| Example Number | Outer Diameter (mm) | Wall Thickness (mm) | Mass/length (g/m) | Density (g/cc) |
|---|---|---|---|---|
| 1 | 15.2 | 0.29 | 10.2 | 0.75 |
| 2 | 15.2 | 0.27 | 7.1 | 0.53 |
| 3 | 15.2 | 0.27 | 10.3 | 0.75 |
| 4 | 15.2 | 0.27 | 7.2 | 0.54 |
| 5 | 15.2 | 0.23 | 5.8 | 0.64 |

Table 2 provides a summary of some of the recorded physical properties of the expanded fluoropolymer tubes.

TABLE 3

Radial Mechanical Testing

| Example Number | Number of Samples Tested | Radial Break strength kN | Radial Break Strength St. Dev. kN | % Radial Elongation |
|---|---|---|---|---|
| 1 | 5 | 36.92 | 0.85 | 1348 |
| 2 | 5 | 21.35 | 0.31 | 1274 |
| 3 | 5 | 36.92 | 1.07 | 1208 |
| 4 | 5 | 21.80 | 0.36 | 1153 |
| 5 | 7 | 38.25 | 2.40 | 64 |

Table 3 provides a summary of some of the radial mechanical testing results.

TABLE 4

Post Radial Stretch Properties

| Example Number | Number of Samples Tested | Mass (g) Average, Std. Dev | Width (mm) Average, Std. Dev | Thickness (mm) Average, Std. Dev | Density (g/cm3) |
|---|---|---|---|---|---|
| 1 | 5 | 0.0649, 0.0003 | 0.77, 0.03 | 0.175, 0.008 | 1.01 |
| 2 | 5 | 0.0454, 0.0001 | 0.68, 0.05 | 0.163, 0.004 | 0.89 |
| 3 | 5 | 0.0651, 0.0004 | 0.85, 0.03 | 0.190, 0.010 | 0.92 |
| 4 | 5 | 0.0460, 0.0002 | 0.80, 0.05 | 0.179, 0.005 | 0.77 |
| 5 | 7 | 0.0370, 0.0003 | 0.68, 0.03 | 0.159, 0.003 | 0.97 |

Table 4 provides the dimensions of the distensible band after being tested according to the radial mechanical test method described herein. The dimensional properties reported in Table 6 were measured approximately in the middle of the length of the broken band.

TABLE 5

Axial Mechanical Testing

| Example Number | Number of Samples Tested | Axial Break strength kN | Standard Deviation kN | % Axial Elongation Average, St. Dev.] |
|---|---|---|---|---|
| 1 | 5 | 1.05 | 0.006 | 37.5, 5.8 |
| 2 | 5 | 0.96 | 0.005 | 38.4, 6.5 |
| 3 | 5 | 1.21 | 0.009 | 56.5, 7.1 |
| 4 | 5 | 1.03 | 0.006 | 52.1, 3.6 |

Table 5 provides summary of some of the axial mechanical testing results.

TABLE 6

Axial and Radial Mechanical Testing Results

| Example Number | Number Tested | Axial Break strength kN | Radial Break strength kN | Axial MTS MPa | Radial MTS MPa | MTS Ratio Axial/Radial |
|---|---|---|---|---|---|---|
| 1 | 5 | 1.05 | 0.0369 | 241 | 31 | 7.9 |
| 2 | 5 | 0.96 | 0.0214 | 312 | 25 | 12.5 |
| 3 | 5 | 1.21 | 0.0369 | 277 | 31 | 9.1 |
| 4 | 5 | 1.03 | 0.0218 | 328 | 25 | 13.1 |

Table 6 provides summary of some of the axial mechanical testing results along with the calculated matrix tensile strength (MTS) ratio.

TABLE 7

Interval Strain Method

| | Matrix Tensile Stress (MPa) Example | | | |
|---|---|---|---|---|
| Strain % | 1 | 2 | 3 | 4 |
| 100 | 7.6 | 6.6 | 7.0 | 6.6 |
| 400 | 36.4 | 35.9 | 35.6 | 34.1 |
| 800 | 150.4 | 175.0 | 152.0 | 187.1 |

Table 7 provides the matrix tensile stress as measured at various strain intervals according to the interval strain method described herein.

TABLE 8A

| | First State | | | After 100% Strain | | | | |
|---|---|---|---|---|---|---|---|---|
| Example Number | Mass (g) Avg. | Thickness (mm) | Width (mm) | Cross Sectional Area mm^2 | Thickness (mm) | Width (mm) | Cross Sectional Area mm^2 | Cross Sectional Area Ratio |
| 1 | 0.0649 | 0.29 | 6.35 | 1.82 | 0.28 | 5.56 | 1.56 | 0.86 |
| 2 | 0.0454 | 0.26 | 6.35 | 1.68 | 0.27 | 5.16 | 1.37 | 0.82 |
| 3 | 0.0651 | 0.27 | 6.35 | 1.72 | 0.27 | 5.56 | 1.49 | 0.86 |
| 4 | 0.0460 | 0.27 | 6.35 | 1.69 | 0.27 | 5.28 | 1.40 | 0.83 |

Table 8A provides the initial dimensions and the dimensions of the distensible band after 100% strain as tested according to the interval strain method described herein.

TABLE 8B

Dimensions at 400% Strain
After 400% Strain

| Example Number | Mass (g) Avg. | Thickness (mm) | Width (mm) | Cross Sectional Area mm^2 | Cross Sectional Area Ratio |
|---|---|---|---|---|---|
| 1 | 0.0649 | 0.24 | 1.59 | 0.38 | 0.20 |
| 2 | 0.0454 | 0.21 | 1.59 | 0.34 | 0.20 |
| 3 | 0.06506 | 0.23 | 1.59 | 0.37 | 0.21 |
| 4 | 0.04598 | 0.23 | 1.59 | 0.37 | 0.22 |

Table 8B provides the dimensions of the distensible band after 400% strain as tested according to the interval strain method described herein.

TABLE 8C

Dimensions at 800% Strain
After 800% Strain

| Example Number | Mass (g) Avg. | Thickness (mm) | Width (mm) | Cross Sectional Area mm^2 | Cross Sectional Area Ratio |
|---|---|---|---|---|---|
| 1 | 0.0649 | 0.19 | 0.80 | 0.15 | 0.08 |
| 2 | 0.0454 | 0.15 | 0.80 | 0.12 | 0.07 |
| 3 | 0.06506 | 0.18 | 0.80 | 0.15 | 0.09 |
| 4 | 0.04598 | 0.16 | 0.80 | 0.13 | 0.07 |

Table 80 provides the dimensions of the distensible band after 800% strain as tested according to the interval strain method described herein.

TABLE 9

| Example # 3 | Cylces to Failure |
|---|---|
| Average | 51,343 |
| St. Dev. | 10,584 |

Table 9 provides a summary of the data recorded from the abrasion test described herein.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A dental cleaning article comprising a substantially circular band of expanded polytetrafluoroethylene having (a) a distensible first state with a first inner diameter that is capable of being distended at room temperature, and (b) a second stretched state having a second inner diameter that is at least two times greater than said first inner diameter, said second stretched state being substantially dimensionally non-recoverable; wherein in said first state said band requires a lower force for distension such that a matrix tensile stress to distend said band is at least approximately 5 MPa and less than 10 MPa and in said second state a higher resistance to strain is exhibited where greater force is required to distend the band providing a tactile limit or stop to alert the user to stop distending the band before breaking occurs, said limit or stop being defined by an inflection point in a stress-strain curve of the article, at which the matrix tensile stress increases quickly; and wherein said inflection point occurs when the matrix tensile stress is approximately 15 MPa.

2. The dental cleaning article of claim 1, wherein the inner diameter of the distensible band in the first state is less than 20 mm.

3. The dental cleaning article of claim 1, wherein the inner diameter of the distensible band in the first state is less than 10 mm.

4. The article of claim 1 wherein the distensible band comprises at least one seam.

5. The article of claim 1 wherein the distensible band of expanded polytetrafluoroethylene is a section of tube.

6. The dental cleaning article of claim 1, wherein the distensible band comprises a sheet band.

7. The dental cleaning article of claim 1, further comprising at least one high density region.

8. The dental cleaning article of claim 1, wherein the matrix tensile stress required to strain the band to at least 200% is less than 15 Mpa.

9. The dental cleaning article of claim 1, wherein the matrix tensile stress required to strain the band to at least 400% is less than 15 Mpa.

10. The dental cleaning article of claim 1, wherein the distensible band of expanded polytetrafluoroethylene has a ratio of matrix tensile strength in two orthogonal directions of at least 5.

11. The dental cleaning article of claim 1, wherein the distensible band in a first state has a first cross-sectional area, and the distensible band in a second stretched state has a second cross sectional area, wherein the first cross sectional area is at least 4 times greater than the second cross-sectional area.

12. The dental cleaning article of claim 1, wherein the distensible band has force to break of at least 20 kN.

13. The dental cleaning article of claim 1, wherein the distensible band has a matrix tensile strength of at least 20 MPa.

14. The dental cleaning article of claim 1, wherein the distensible band has an abrasion cycles to failure of at least 30,000.

15. The dental cleaning article of claim 1, wherein the distensible band of expanded polytetrafluoroethylene in a first state has a first microstructure of irregularly shaped nodes and interconnecting fibrils; and a second stretched state having a second microstructure of nodes having an aspect ratio of at least 10 and interconnecting fibrils.

16. The dental cleaning article of claim 15, wherein the first microstructure of irregularly shaped nodes comprise nodes having an aspect ratio of no more than 5.

17. The dental cleaning article of claim 15, wherein the second microstructure of nodes have an aspect ratio of at least 20.

18. The dental cleaning article of claim 15 wherein the second microstructure comprises nodes that are aligned essentially parallel.

19. A dental cleaning article comprising a distensible substantially circular band of expanded polytetrafluoroethylene having:
  (a) a first state with a first circumference and a first cross-sectional area; and
  (b) a second stretched state having a second circumference and a second cross-sectional area;
wherein said second circumference is at least two times greater than said first circumference,
and said second stretched state being substantially dimensionally non-recoverable,
wherein in said first state said band requires a lower force for distension such that a matrix tensile stress to distend said band is at least approximately 5 MPa and less than 10 MPa and in said second state a higher resistance to strain is exhibited where greater force is required to distend the band providing a tactile limit or stop to alert the user to stop distending the band before breaking occurs, said limit or stop being defined by an inflection point in a stress-strain curve of the article, at which the matrix tensile stress increases quickly; and wherein said inflection point occurs when the matrix tensile stress is approximately 15 MPa.

20. The article of claim 19, wherein the band of expanded polytetrafluoroethylene further comprises at least one seam.

21. The article of claim 19, where-in the band of expanded polytetrafluoroethylene is a section of tube.

22. The article of claim 19, where-in the band of expanded polytetrafluoroethylene is a sheet band.

23. The article of claim 19, wherein the band of expanded polytetrafluoroethylene in a first state, further comprises at least one high density region.

24. The article of claim 19, wherein the second circumference is at least four times greater than said first circumference.

25. The article of claim 19, wherein the second cross-sectional area is no more than one quarter the said first cross-sectional area.

26. A dental cleaning article comprising:
  a. a distensible substantially circular band of expanded polytetrafluoroethylene having a first state with a first circumference wherein the band of expanded polytetrafluoroeythlene is capable of being distended to a second stretched state having a second circumference wherein said second circumference is at least two times greater than said first circumference and wherein said second stretched state is substantially dimensionally non-recoverable; wherein in said first state said band requires a lower force for distension such that a matrix tensile stress to distend said band is at least approximately 5 MPa and less than 10 MPa and in said second state a higher resistance to strain is exhibited where greater force is required to distend the band providing a tactile limit or stop to alert the user to stop distending the band before breaking occurs, said limit or stop being defined by an inflection point in a stress-strain curve of the article, at which the matrix tensile stress increases quickly; and wherein said inflection point occurs when the matrix tensile stress is approximately 15 MPa; and
  b. a support device comprising:
    i. a first and second support member;
    ii. a pivot; and
    iii. a securing portion,
  whereby the distensible band can be secured by the securing portion, and the first and second support members can be manually manipulated to cause the support members to pivot and stretch the band.

27. The article of claim 26 wherein the securing portion comprises at least one recess in a support member.

* * * * *